United States Patent
Hilgers et al.

(10) Patent No.: US 10,342,867 B2
(45) Date of Patent: Jul. 9, 2019

(54) ADJUVANTS

(71) Applicant: LiteVax B.V., Ophemert (NL)

(72) Inventors: Lucas A. Th. Hilgers, Ophemert (NL); Peter Paul L. I. Platenburg, Cothen (NL); Johannes F. Van Den Bosch, Boxmeer (NL)

(73) Assignee: LITEVAX B.V., Ophemert (NL)

( * ) Notice: Subject to any disclaimer, the term of this patent is extended or adjusted under 35 U.S.C. 154(b) by 0 days.

(21) Appl. No.: 15/328,407

(22) PCT Filed: Jul. 24, 2015

(86) PCT No.: PCT/NL2015/050544
§ 371 (c)(1),
(2) Date: Jan. 23, 2017

(87) PCT Pub. No.: WO2016/013938
PCT Pub. Date: Jan. 28, 2016

(65) Prior Publication Data
US 2017/0209568 A1 Jul. 27, 2017

(30) Foreign Application Priority Data
Jul. 24, 2014 (NL) .................................. 2013257

(51) Int. Cl.
| A61K 39/00 | (2006.01) |
|---|---|
| A61K 39/39 | (2006.01) |
| C07H 15/06 | (2006.01) |
| C12N 7/00 | (2006.01) |
| A61K 39/145 | (2006.01) |

(52) U.S. Cl.
CPC ............ *A61K 39/39* (2013.01); *A61K 39/145* (2013.01); *C07H 15/06* (2013.01); *C12N 7/00* (2013.01); *A61K 2039/55566* (2013.01); *A61K 2039/55572* (2013.01); *C12N 2760/16134* (2013.01)

(58) Field of Classification Search
None
See application file for complete search history.

(56) References Cited

U.S. PATENT DOCUMENTS

2003/0220270 A1* 11/2003 Hilgers ................ A61K 9/0019
514/23
2005/0245463 A1 11/2005 Pham et al.

FOREIGN PATENT DOCUMENTS

| EP | 0 800 539 B1 | 9/2003 |
| EP | 2 580 226 A1 | 4/2013 |
| WO | WO-96/20222 A1 | 7/1996 |
| WO | WO-01/40240 A2 | 6/2001 |
| WO | WO-2011/155822 A1 | 12/2011 |

OTHER PUBLICATIONS

Layre, Journal of Lipid Research, vol. 52, 2011, pp. 1098-1110. (Year: 2011).*
Hamasaki, Infection and Immunity, Jun. 2000, p. 3704-3709. (Year: 2000).*
Hilgers et al., "Sulfolipo-cyclodextrin in squalane-in-water as a novel and safe vaccine adjuvant", Vaccine, vol. 17, 1999, pp. 219-228.
Hilgers, "Large animal-model for establishing E/T ratio of adjuvants", Chapter 17, Methods in Molecular Biology, vol. 626, 2010, pp. 251-259.
Turkstra et al., "Pharmacological and toxicological assessment of a potential GnRH vaccine in young-adult male pigs", Vaccine, vol. 29, 2011, pp. 3791-3801.
Ryll et al.,"Mycobaterial cord factor, but not sulfolipid causes depletion of NKT cells and upregulation of CD1d1 on murine macrophages", Microbes and Infection, 2001, vol. 3, pp. 611-619.
Sahara et al., "Anti-tumor effect of chemically synthesized sulfolipids based on sea urchin's natural sulfonoquinovosylmonoacylglycerols", Japanese Journal of Cancer Research, Jan. 2002, vol. 93, pp. 85-92.
International Search Report issued in International Patent Application No. PCT/NL2015/050544, dated Sep. 18, 2015.

* cited by examiner

*Primary Examiner* — Layla D Berry
(74) *Attorney, Agent, or Firm* — Sunit Talapatra; Foley & Lardner LLP

(57) ABSTRACT

The present invention relates to a family of carbohydrate monosulphate fatty acid esters, which contain less than 10 mole % of carbohydrate polysulphate fatty acid esters, and to a method of preparation thereof. The monosulphate carbohydrate esters according to the invention comprise one sulphate ester and at least one fatty acid and are among others useful as adjuvants for immunological products such as vaccines.

34 Claims, 7 Drawing Sheets

ADJUVANTS

CROSS-REFERENCE TO RELATED APPLICATIONS

This application is the National Phase of International Patent Application No. PCT/NL2015/050544, filed Jul. 24, 2015, published on Jan. 28, 2016 as WO 2016/013938 A1, which claims priority to Netherlands Patent Application No. 2013257, filed Jul. 24, 2014. The contents of which are herein incorporated by reference in their entirety.

FIELD

The present invention is in the field of sulphated carbohydrate fatty acid esters as vaccine adjuvants.

BACKGROUND

Vaccination is one of the most cost-effective means to prevent and to control infectious diseases in both human and animal health. Vaccines contain either modified live antigens such as bacteria, viruses, parasites, recombinant (micro-) organisms or inactivated (non-replicating) antigens such as inactivated viruses, inactivated bacteria, inactivated parasites, subunits of infectious (micro-) organisms, proteins, polysaccharides, peptides, glycoproteins, polysaccharide-protein conjugates, peptide-protein-conjugates, etc. In many cases, the immune response against antigens is too low. In such cases, an adjuvant can be added to stimulate the immune response, and thereby increase the protective action of vaccines.

In the control of existing, emerging and re-emerging infectious diseases, adjuvants play a decisive role. Adjuvants may have different functions such as to increase (protective) immune response, to direct the type of response, to increase the duration of (protective) immunity, to reduce the lag-time to (protective) immunity, to reduce the dose of antigen required and reduce the number of vaccinations needed. By combining an antigen with an adjuvant, levels of immunity may be reached that can not be reached by treatment with antigen alone.

Also, an adjuvant may reduce significantly the dose of antigen needed to reach predefined levels of protection, thereby reducing the costs of goods, transport and storage and increasing production capacity and availability. The inexpensive adjuvant replaces a large portion of the expensive antigen and promotes access to these medicinal products to the poor.

Alum (aluminium hydroxide) is the classical example of a safe adjuvant and is applied in several human vaccines. However, in many cases the adjuvant activity is insufficient and a stronger but at least as safe adjuvant is needed.

Furthermore, sulphate-substituted carbohydrate fatty acid ester derivatives are known. These are commonly called sulpholipid-carbohydrates (SL-carbohydrates), and their synthesis and function as adjuvant are known.

The known SL-carbohydrates have in common that they are prepared by two synthesis steps, an esterification of the hydroxyl-groups of the carbohydrate with the fatty acid(s) and an esterification of the hydroxyl-groups of the carbohydrate with a sulphonating agent. These reactions may be performed simultaneously or in any order. Both reactions are ad random reactions, which means that there is no or limited discrimination between the different hydroxyl groups of the carbohydrate available for esterification. Therefore, the sulphate group(s) and the fatty acid(s) are distributed randomly over the substituted carbohydrate, resulting in a mixture of many different chemical compounds.

The number of chemically distinct SL-carbohydrates formed by ad random synthesis methods depends on the number of reactive sites (hydroxyl groups) on the carbohydrate backbone. Contacting a carbohydrate with 1 equivalent (one mole per mole of carbohydrate) of sulphonating agent results in the formation of carbohydrates with a different number of sulphate groups and in the formation of carbohydrates with sulphate groups at the different positions. For example, SL-carbohydrate mixtures known in the art consist of a mixture of carbohydrate esters, among others with no sulphate group (herein referred to as 'ZERO'), one sulphate group (herein referred to as 'MONO') or multiple sulphate groups (two or more sulphate groups; herein referred to as 'POLY'). The ratio of ZERO:MONO:POLY can be determined statistically by using the formula disclosed in WO 96/20222. At 1 mole of sulphonating agent per mole of disaccharide (with eight hydroxyl groups available for sulphonation), the theoretical molar ratio of ZERO:MONO:POLY in the final product is 37%:37%:26%. At lower molar ratio of sulphonating agent per carbohydrate, the % POLY formed decreases, and the % ZERO formed increases. At 0.2 mole of sulphonating agent per mole of carbohydrate, the theoretical molar ratio of ZERO:MONO:POLY is 82%:16%:2%.

The use of a mixture of components as a medicinal product may be associated with important drawbacks with respect to quality, consistency and safety of the product. In particular for adjuvants in e.g. vaccines, it is important to emphasize that they are applied at a large scale in healthy subjects. Toxicity, efficacy and quality are therefore important prerequisites.

It is generally accepted that there is a relationship between adjuvant activity (efficacy) and side effects (toxicity) and that increasing efficacy is accompanied by increasing toxicity (see e.g. Hilgers, Methods Mol. Biol. 626 pp. 251-9, 2010). The ratio between efficacy and toxicity is called the E/T ratio, and is an important parameter in defining adjuvants. A drawback of adjuvants comprising a SL-carbohydrate of the prior art is the lack of sufficient safety (too high toxicity or a too low E/T-ratio).

Adjuvant activity and toxicity increase with increasing dose of the adjuvant. By decreasing the dose of adjuvant, the side effects decrease also. However, it is uncertain whether at a level of acceptable toxicity, sufficient efficacy remains. Therefore, there is still a need for adjuvants with a higher efficacy/toxicity-ratio than that of the existing ones, including the SL-carbohydrate-based adjuvants. These improvements may include higher efficacy with similar toxicity, lower toxicity with similar efficacy or higher efficacy combined with lower toxicity.

WO 01/402490 discloses SL-monosaccharides and SL-disaccharides, a method for preparing these SL-monosaccharides and SL-disaccharides and their use as vaccine adjuvant. SL-disaccharide mixtures are formed in a reaction with one molar equivalent of sulphonating agent per mole of disaccharide and seven molar equivalents of fatty acid chlorides (also referred to as acyl chlorides or acoylchloride) per mole of disaccharide. This results in a mixture of 6,561 different possible chemical compounds, the relative presence of which can be determined by statistics. These products have been subject of intense research under the name 'CoVaccine HT' (BTG plc, UK). Mixtures obtained by using one or more molar equivalents of sulphonating agent and one or more molar equivalents of fatty acid chloride were tested for their adjuvant activity. However, the toxicity of the tested SL-carbohydrate derivatives was too high for the wide-spread use in humans.

Hilgers et al. (Vaccine 17, pp. 219-228, 1999), Blom & Hilgers (Vaccine 29, pp. 3791-3801, 2011) and EP2580226 disclose undesired side effects such as body temperature rise and local irritation of SL-carbohydrate-based adjuvants and/or vaccines.

Hilgers et al. (Vaccine 17, pp. 222-225, 1999) discloses a relationship between the molecular weight of the SL-carbohydrates on the one hand and adjuvant activity and local reactogenicity at the other. The local reaction but not the adjuvant activity increases with increasing molecular weight of the SL-carbohydrate. Also, a transient increase in body temperature of up to 1.7° C. and swelling at the injection site for up to 4 weeks is very common. Vomiting occurs in 1-25% of cases during the first hour after vaccination. Persistent mild to moderate granulomatous inflammation of the muscular fibers is observed at the injection side up to 8 weeks after vaccination (European Public Assessment Report (EPAR) on porcine circovaccine adjuvanted with SL-cyclodextrin).

EP2580226 discloses adverse events of SL-trisaccharides including local adverse reaction and rise in body temperature. The side effects are significant and prohibit widespread prophylactic application of the product in healthy subjects. Also for a SL-disaccharide, significant local and systemic side-effects were observed also as disclosed by Turkstra et al. (Vaccine 29, pp. 3791-3801, 2011) and EP2580226.

Human clinical trials using SL-disaccharide (CoVaccine HT) have been discontinued for reasons which can be related to or the consequence of the adverse reactions noted with SL-carbohydrates in general, including SL-disaccharides. The known SL-carbohydrate-based adjuvants are considered unsuitable for human use.

WO 2008/005824 discloses compositions comprising natural killer T cell agonists and physiological acceptable vehicles, and methods of stimulating an natural killer T cell and enhancing an immune response. The compounds disclosed are synthetic derivatives of monosaccharide and disaccharide containing a ceramide group and optionally one or multiple sulphate groups. The compounds do not comprise a fatty acid on the saccharide core, and are therefore distinct from the presently claimed compounds.

WO 01/402490 discloses methods to isolate a mixture of SL-monosaccharide and SL-disaccharide derivatives from the reaction mixture. The techniques listed include crystallization, precipitation, filtration, evaporation dialysis or ultrafiltration. Although these methods may be suitable to isolate a mixture of SL-monosaccharide and SL-disaccharide derivatives from the reaction mixture or to separate a mixture of SL-monosaccharide and SL-disaccharide derivatives from certain by-products, they are not suitable to purify MONO isomers of the SL-carbohydrates of the present invention from POLY isomers.

In summary, a drawback of strong adjuvants such as SL-carbohydrate-based products is their relatively high toxicity and a drawback of safe adjuvants such as alum is their relatively low adjuvant activity.

As such, there remains a need for adjuvants with a higher efficacy at the same or lower toxicity, to allow for further increasing the immune response during vaccination. The present invention discloses compounds which achieve that.

BRIEF DESCRIPTION OF THE FIGURES

FIG. 4: Photographs of the site of injection one week after the second immunization in one rabbit that received MONO, G10-MONO, as adjuvant (FIG. 4a) and 8 rabbits that received POLY, either G10-POLY or M10-POLY, as adjuvant (FIG. 4b-4i).

DETAILED DESCRIPTION

Figure 1:
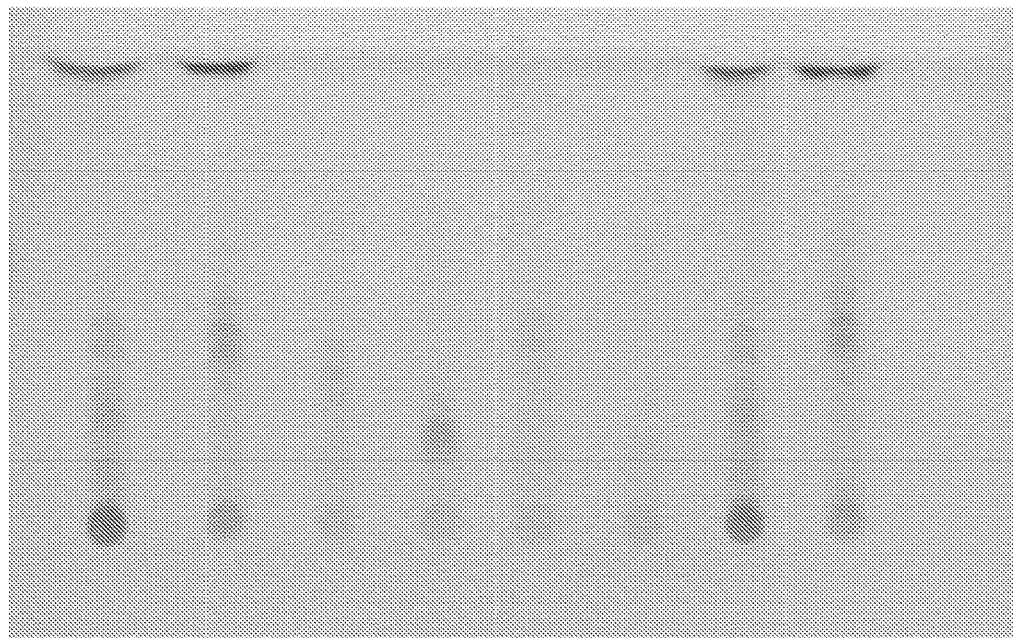
FIG. 1: High performance thin layer chromatography (HPTLC) of adjuvant formulations tested in rabbits of SL-carbohydrates of the prior art and of carbohydrate ester mixtures enriched in MONO of the present invention. From left to right: CoVaccine HT (prepared by CoVaccine BV), S12 (CoVaccine HT-like formulation prepared in-house), M10-MONO (isolated from M10), G12-MONO (isolated from G12), M12-MONO (isolated from M12), squalane-in-water emulsion without a SL-carbohydrate, CoVaccine HT (duplicate), and S12 (duplicate).

In view of the foregoing it is an object of the present invention to provide an adjuvant, which has an excellent safety and efficacy profile, which is easy and inexpensive to prepare, and which has a high quality and stability. It is a further object of the present invention to provide compounds that can be used in an adjuvant composition, for example in combination with an antigenic component to prepare a vaccine.

The present invention pertains to an adjuvant comprising a carbohydrate ester mixture comprising a sulpholipid-carbohydrate, which is a carbohydrate substituted with at least one sulphate group and with at least one fatty acid, wherein less than 10 mol % of the carbohydrate ester mixture is substituted with more than one sulphate group, and a pharmaceutically acceptable carrier. Preferably, the carbohydrate mixture comprises less than 50 mole % of a carbohydrate ester without sulphate groups, more preferably 25 mole % or less, even more preferably less than 10 mole %.

Preferably, less than 5 mole %, more preferably less than 2% and most preferably around 0% of the carbohydrate ester mixture is substituted with more than one sulphate group.

In the present invention, it has been found that the toxicity of a sulpholipid carbohydrate mixture such as CoVaccine HT was largely due to the group of sulpholipid carbohydrates substituted with more than one sulphate group (referred to as "POLY"). Sulpholipid carbohydrates substituted with one sulphate group (referred to as "MONO") display good adjuvant activity, while having considerably less toxicity. As such, the efficacy/toxicity ratio of a carbohydrate ester mixture enriched in MONO, is improved. As discontinuation of the human trials with CoVaccine HT was at least partly due to unacceptable high toxicity of POLY as one of the major constituents of CoVaccine HT, substantial removal of POLY from the mixture should result in acceptable toxicity in new human trials.

A carbohydrate, in the present context, is a monosaccharide, a disaccharide, a trisaccharide or a linear or cyclic polysaccharide, preferably with at least 4 and no more than 10 monosaccharide units. Preferably, a carbohydrate is a monosaccharide, a disaccharide, a trisaccharide, a cyclodextrin or a mixture thereof, more preferably a monosaccharide, a disaccharide or a cyclodextrin or a mixture thereof, even more preferably a disaccharide and/or a monosaccharide, and most preferably the carbohydrate is a disaccharide.

A monosaccharide is a sugar selected from pentoses with the general formula $C_5H_{10}O_5$ and from hexoses with the general formula $C_6H_{12}O_6$. Alternatively, a monosaccharide is one or more selected from the group consisting of allose, altrose, glucose, mannose, gulose, idose, galactose, talose, psicose, fructose, sorbose, tagatose, arabinose, ribose, xylose, lyxose, ribulose, xylulose and inositol. Preferably, a monosaccharide is one or more selected from fructose, galactose and glucose.

A disaccharide is a sugar with the general formula $C_{12}H_{22}O_{11}$, and is preferably one or more selected from the group consisting of sucrose, maltose, lactose, lactulose, cellobiose, trehalose, gentiobiose, turanose, isomaltulose and melibiose. Preferably, a disaccharide is one or more selected from lactose, maltose and sucrose. Most preferably, a disaccharide is maltose and/or lactose.

A trisaccharide is a sugar with the general formula $C_{18}H_{32}O_{16}$ and is preferably one or more selected from the group consisting of raffinose, melezitose, maltotriose, isomaltotriose, raffinose, kestose and negerotriose. Preferably, a trisaccharide can be selected from raffinose, melezitose and/or maltotriose. Most preferably, a trisaccharide is selected from raffinose and/or maltotriose.

A cyclodextrin is a cyclic polysaccharide with a various number of monosaccharides as defined above. A cyclodextrin is preferably an α-, β- or γ-cyclodextrin (6, 7 or 8 sugar units, respectively).

A carbohydrate ester in the present context is a substituted carbohydrate. Substitution means that other groups are attached to the carbohydrate through the hydroxyl-groups of the carbohydrate via an ester bond, so that the substituted carbohydrates in the present context are carbohydrate esters. Substitution is with a sulphate group, and with at least one fatty acid. Thus, sulphate groups are covalently bound to the carbohydrate through an ester group on a carbohydrate hydroxyl group, and similarly, fatty acids are covalently bound to the carbohydrate through an ester group on a carbohydrate hydroxyl group.

A carbohydrate ester without sulphate groups in the present context is a carbohydrate ester, substituted with one or more fatty acids, but not substituted with a sulphate group.

A sulpholipid carbohydrate in the present context is a carbohydrate substituted with at least one sulfate group and with at least one fatty acid. The carbohydrate ester mixture of the invention is enriched in monosulphate carbohydrate fatty acid esters, and comprises less than 10 mol % of carbohydrate esters substituted with more than one sulphate group.

As such, the present invention relates to an adjuvant composition comprising a carbohydrate ester mixture enriched in monosulphate carbohydrate fatty acid ester, and its use as an adjuvant in for instance vaccines.

A carbohydrate ester mixture according to the invention comprises a carbohydrate substituted on a hydroxyl-group with a sulphate group ($—SO_3^-$). A sulphate group in the present context may comprise a neutral or ionic substituent, selected from the group consisting of atoms and/or molecules that form monovalent cations. Examples of members of this group include $H^+$, $Na^+$, $K^+$, $Li^+$ and $NH_4^+$ and triethylammonium ($Et_3NH^+$). Thus, a sulphate group can for example be $—SO_3^-$, $—SO_3H$, $—SO_3Na$, $—SO_3K$, $—SO_3Li$ or $—SO_3NH_4$.

In addition, the carbohydrate is substituted on a hydroxyl-group with at least one fatty acid per molecule of carbohydrate. Preferably, the carbohydrate is substituted with a multitude of fatty acids, such as 2-4 for monosaccharides, 2-7 for disaccharides or even more for larger carbohydrates as defined above. More preferably, substantially all of the hydroxyl groups of the carbohydrate, not substituted with sulphate groups, are substituted with fatty acids. This means that the carbohydrate is preferably substantially saturated with fatty acids, in addition to the presence of a sulphate group. Substantially, in this respect, means that of all hydroxyl groups not substituted with sulphate on a single carbohydrate molecule, at least 50%, preferably at least 75%, more preferably at least 80% or at least 90%, and even more preferably at least 95% is substituted with a fatty acid.

As such, the carbohydrate ester mixture of the invention is a mixture enriched in a carbohydrate substituted with one sulphate group and at least one fatty acid (i.e. enriched in monosulphate carbohydrate fatty acid ester). Preferably the carbohydrate ester mixture of the invention comprises carbohydrates wherein one of the hydroxyl-groups of the carbohydrate is substituted with a sulphate group, and wherein substantially all of the remaining hydroxyl-groups of the carbohydrate are substituted with fatty acids. The carbohydrate ester mixture of the invention comprises less than 10 mol % of carbohydrates substituted with more than one sulphate group.

Fatty acids, in the present context, are well known in the art, and can be any fatty acid. Generally a fatty acid in the present context can be a fatty acid which has between 6 and 18 carbon atoms, preferably between 8 and 12 carbon atoms. Fatty acids may be saturated or unsaturated, and may be branched, but are preferably linear. Generally, a fatty acid can be a saturated fatty acid according to general formula —O—(C=O)—$(CH_2)_x$—$CH_3$ wherein x is between 4 and 16. Furthermore, a fatty acid can be an unsaturated fatty acid according to one of the formulas —O—(C=O)—$(CH_2)_x$—CH=CH—$(CH_2)_y$—$CH_3$ wherein x+y is between 4 and 14, or —O—(C=O)—$(CH_2)_y$—CH=CH—$(CH_2)_y$—CH=CH—$(CH_2)_z$—$CH_3$ wherein x+y+z is between 2 and 12.

Preferably, fatty acids may be of the general structure of —O—(C=O)—$(CH_2)_x$—$CH_3$ wherein x may be 4 (hexanoic acid), 6 (octanoic acid), 8 (decanoic acid), 10 (dodecanoic acid; also referred to herein as lauric acid), 12 (tetradecanoic acid also known as myristic acid) or 14 (hexadecanoic acid also known as palmitic acid). Further preferred are fatty acids with the general structure of —O—(C=O)—$(CH_2)_x$—CH=CH—$(CH_2)_y$—$CH_3$ wherein x+y may be 14 (for example oleic acid). Further preferred are fatty acids with the general structure of —O—(C=O)—$(CH_2)_x$—CH=CH—$(CH_2)_y$—CH=CH—$(CH_2)_x$—$CH_3$ wherein x+y+z is 12 (for example linoleic acid). Preferably, the fatty acid is linear, and has between 6 and 18 carbon atoms, more preferably between 8 and 12. Most preferably, the fatty acid is decanoic acid or dodecanoic acid.

When a carbohydrate is substituted with more than 1 fatty acid, any combination of fatty acids as described above is possible. Generally, any combination of features described herein is considered as described in the context of the present invention.

It is generally known that when making carbohydrates substituted with one or more sulphate groups and with fatty acids, the reactions required for the formation of these compounds proceed at random. As such, in the process of transforming a carbohydrate with N hydroxyl-groups to a carbohydrate substituted with a sulphate group and with at least one fatty acid, the result is not a single molecular species defined by the carbohydrate and the quantity of added sulphate and fatty acids. Instead, a mixture of different carbohydrates is obtained, wherein the individual carbohydrate molecules may contain from 0-N sulphate groups, from 0-N fatty acid groups, and from 0-N unreacted (free) hydroxyl-groups.

The carbohydrates of the present invention are formed by procedures similar to those described in WO 01/40240. However, a difference with WO 01/40240 is that the carbohydrate ester mixture of the invention is subsequently enriched in carbohydrate substituted with one sulphate group and with at least one fatty acid by fractionation, such that less than 10 mol % of the carbohydrate ester mixture is substituted with more than one sulphate group. Preferably, less than 5 mol % of the carbohydrate is substituted with more than one sulphate group, more preferably, less than 2 mol % is substituted with more than one sulphate group and even more preferably, essentially all sulphate carbohydrate esters in the carbohydrate ester mixture are substituted with a single sulphate group.

An effect of this difference is that the efficacy of the carbohydrate as an adjuvant remains stable or is increased, whereas the toxicity is substantially lower or even absent. Thus, an adjuvant with a considerably improved E/T-ratio is obtained, relative to known adjuvants, among which SL-carbohydrate-based adjuvants.

Therefore, the present invention relates among others to a method to prepare a carbohydrate ester mixture comprising monosulphate carbohydrate fatty acid esters (herein referred to as 'MONO'). The method includes synthesis of a mixture of sulpho- and fatty acid-substituted carbohydrates. Sulpho and fatty acid substituted carbohydrates are also called sulpholipid-carbohydrates (SL-carbohydrates). Subsequently, a carbohydrate ester mixture enriched in SL-carbohydrate substituted with one sulphate group and with at least one fatty acid (enriched in monosulphate carbohydrate fatty acid ester) is isolated from the carbohydrate ester mixture by fractionation.

As such, the invention further pertains to a process for preparing a carbohydrate ester mixture comprising a monosulphate carbohydrate fatty acid ester, wherein less than 10 mol % of the carbohydrate ester mixture is substituted with more than one sulphate group and wherein preferably less than 50 mole % of the carbohydrate ester mixture is a carbohydrate ester without sulphate groups, comprising esterification and fractionation of a carbohydrate, wherein the esterification comprises reaction of a carbohydrate with a sulfonating agent and with a reactive fatty acid acyl compound to obtain the carbohydrate ester mixture, and wherein fractionation comprises removal of carbohydrate esters with more than one sulphate group from the carbohydrate ester mixture to obtain said mixture comprising monosulphate carbohydrate fatty acid ester. Preferably, fractionation also comprises removal of carbohydrate esters without sulfate groups from the carbohydrate ester mixture.

Preferably, less than 5 mol % of the carbohydrate ester mixture is substituted with more than one sulphate group, more preferably less than 2%, and even more preferably around 0%. Further preferably, the carbohydrate ester mixture comprises less than 50 mole %, preferably 25 mole % or less, even more preferably less than 10 mole % of a carbohydrate ester without sulphate groups. In addition, the invention pertains to the mixture enriched in monosulphate carbohydrate fatty acid ester obtainable by this method for use as an adjuvant, and to an adjuvant, comprising the thus obtained mixture enriched in monosulphate carbohydrate fatty acid ester.

Substitution of the carbohydrate occurs through esterification of the carbohydrate, preferably in solution, of one or more of the free hydroxyl groups of the carbohydrate. This results in a carbohydrate ester.

Substitution with a sulphate group occurs through reaction of a sulphonating agent with the carbohydrate. Preferred sulphonating agents are gaseous $SO_3$, $HClSO_3$ (chlorosulphonic acid), $SO_3$-pyridine, $SO_3$-2-methylpyridine, $SO_3$-2,6-dimethylpyridine, $SO_3$-dimethylformamide, $SO_3$-trimethylamide, $SO_3$-triethylamine, $SO_3$-dimethylanaline, $SO_3$—N— ethylmorpholine, $SO_3$-diethylanaline and $SO_3$-dioxane. Most preferred are $SO_3$-pyridine and $SO_3$-triethylamine.

Substitution with a fatty acid occurs through reaction of the analogous reactive acyl compound, i.e. a reactive fatty acid acyl compound, with the carbohydrate. The reactive fatty acid acyl compound may be a fatty acid chloride, bromide or iodide, a fatty acid thioester, fatty acid anhydride or a fatty acid ester. Preferably, the reactive fatty acid acyl compound is a fatty acid halide, anhydride or thioester, more preferably a fatty acid chloride (sometimes called an acoyl chloride or an acyl chloride).

Highly preferred reactive fatty acid acyl compounds are hexanoylchloride, octanoylchloride, decanoylchloride, dodecanoylchloride (lauroylchloride), tetradecanoylchloride (myristoylchloride), hexadecanoylchloride (p almitoylchloride) and octadecanoylchloride (stearoylchloride and oleoylchloride). Most preferred are decanoylchloride or dodecanoylchloride.

A preferred solvent for substitution is a polar solvent, preferably a polar aprotic solvent. Further preferably, the solvent is anhydrous.

Preferably, the solvent is pyridine, dimethylformamide, N-methylpyrrolidinone, dimethylsulfoxide, acetonitrile, nitromethane or a mixture thereof. Preferably, the solvent is pyridine, dimethylformamide, N-methylpyrrolidinone or a mixture thereof, and most preferably the solvent is a mixture of anhydrous pyridine and anhydrous dimethylformamide.

The reaction is generally done in as small a volume of solvent as possible. Preferably, the volumetric amount of solvent is approximately equal to the amount of reactive acyl compound, such as fatty acid chloride. Preferably, the solvent(s) is/are chosen such that the solvent can be easily removed from the reaction mixture, by for instance precipitation, filtration, crystallization or evaporation.

Substitution with the reactive acyl compound is preferably carried out for a period of 4 to 8 hours, preferably about 6 hours, at a temperature of about 60 to 70° C. It may be desired to let the reaction mixture stand hereafter for up to 18 hours at ambient temperature.

The reaction with the sulphonating agent(s) is preferably carried out for a period of 1 to 4 hours at between ambient temperature and 70° C. It may be desired to let the reaction mixture stand hereafter for up to 18 hours at ambient temperature.

In one embodiment the carbohydrate is first reacted with a sulphonating agent at ambient temperature and subsequently the temperature is brought to about 50-70° C., preferably 55-70° C. and more preferably to about 60° C. for reaction with the reactive acyl compound. In this regard, it is noted that the temperature is not critical to the process. Such a feature permits the process to be performed at a wide range of temperatures and under a wide range of conditions with concomitant savings. It is contemplated that an ambient temperature as low as about 10° C. could be acceptable. Preferred ambient temperatures are not lower than about 15° C., more preferably not lower than about 18° C. Further, ambient temperatures for reaction with the sulphonating agent are preferably not higher than about 50° C., more preferably not higher than about 40° C., most preferably not higher than about 25° C.

The carbohydrate may be reacted first with a sulphonating agent and then with at least one fatty acid chloride or vice versa. Preferably, the carbohydrate is reacted first with the sulphonating agent and then with the reactive acyl compound. Further preferably, the carbohydrate is reacted with a quantity of the sulphonating agent giving the maximal yield of carbohydrate monosulphate. For anhydrous carbohydrates, this is one mole of sulphonating agent per mole of carbohydrate. For carbohydrate monohydrates, this is between one and two mole of sulphonating agent per mole of carbohydrate.

As has been mentioned, it is preferred that as small an amount of solvent as possible is used. In this respect it is preferred that the carbohydrate is dissolved in the solvent(s) by heating resulting in a transparent, homogeneous solution. In particular, this method of preparing a homogenous solution is suitable for carbohydrates which are relatively poorly soluble in the organic solvent(s) or are difficult to dissolve in the organic solvents, for example sucrose and lactose. To dissolve these carbohydrates in the least quantity or volume of organic solvents, the temperature is preferably increased to more than 80° C., more preferably to more than 90° C.

In a preferred embodiment, after the substitution is completed, the substituted carbohydrates in the organic solvent(s) are neutralized with a solution of an inorganic or organic base, such as NaOH, $NH_4OH$, KOH, triethylamine or ammonia.

The substituted carbohydrates may be recovered by cooling, resulting in the formation of two or three or more distinct phases of which one is rich in the substituted carbohydrate. This can be recovered by methods well known in the art including filtering, decanting, evaporation, extraction and the like. Residual solvents and other compounds are removed from this phase by for example evaporating at increased temperature and reduced pressure, or washing with an aqueous phase.

At this stage, the substituted carbohydrate comprises a mixture of different carbohydrate esters, substituted randomly with a varying number of sulphate groups, and a varying number of fatty acids, as described above. In all cases, the carbohydrate is substituted with at least one fatty acid, i.e. the unreacted carbohydrate is essentially absent.

The carbohydrate ester mixture thus can comprise:
MONO is a carbohydrate ester, which is substituted with one sulphate group per molecule of carbohydrate and with at least one fatty acid ester (a monosulphate carbohydrate fatty acid ester).
POLY is a carbohydrate ester, which is substituted with more than one sulphate group per molecule of carbohydrate and with at least one fatty acid ester.
ZERO is a carbohydrate ester with at least one fatty acid ester but which does not contain sulphate groups.

Preferably, a carbohydrate ester mixture of the invention comprises less than 10 mole % of POLY. More preferably, said mixture comprises less than 5 mol % of POLY or even more preferably, said mixture comprises less than 2 mol % of POLY. Most preferably, said mixture comprises no detectable POLY (around 0% POLY).

Further preferably, said mixture comprises less than 50 mole % ZERO, more preferably 25 mole % or less, even more preferably less than 10 mole % of ZERO.

The carbohydrate ester mixture is enriched in MONO by fractionation of the reaction mixture comprising the SL-carbohydrate mixture. Fractionation can be done by purification methods known in the art such as liquid extraction, liquid chromatography, crystallization, electrophoresis, supercritical extraction or a combination of such methods. Preferably, the carbohydrate ester mixture enriched in MONO is isolated by liquid extraction or liquid chromatography. More preferably, the carbohydrate ester mixture of the invention is isolated by liquid chromatography.

The stationary phase of the liquid chromatography may be silica, modified silica, alumina, Florisil, anion-exchange resins for example resins available under the tradename Amberjet™, Amberset™ and Dowex™ of Dow Chemical Company.

The mobile phase of the liquid chromatography (the 'eluent') may be a single solvent or a mixture of two or more solvents selected from organic liquids known in the art, such as n-hexane, n-heptane, isopropanol, ethanol, methanol, triethylamine, trimethylamine, ammonia and water. Preferably, the solvents are safe as for example evidenced by the classification by registration authorities (e.g. FDA or EMA) as 'solvents to be limited' or 'solvents with low toxic potential'. A preferred solvent is a mixture of n-heptane, isopropanol and triethylamine, preferably at volume ratio of between 90:5:5 and 50:30:20.

The carbohydrate ester mixture of the invention is isolated from the reaction mixture after completion of the synthesis or from an extract thereof. Preferably, it is isolated from an extract of the reaction mixture containing a mixture of substituted carbohydrates and by-products. The extract can be obtained by liquid-liquid extraction or differential precipitation.

A preferred method is the extraction of the reaction mixture by an organic solvent such as n-heptane or n-hexane. More preferred is extraction with n-hexane or n-heptane of the reaction mixture supplemented with an aqueous phase to promote phase separation.

The reaction mixture or extract from which the carbohydrate ester mixture of the invention is to be isolated is preferably dissolved or diluted in the eluent (mobile phase) used for the liquid chromatography.

The volume of reaction mixture or extract to be fractionated is between 1/10 and 1/100 of the column volume used for the liquid chromatography. The column is eluted with 1-10 times of volume of the column. The elution may be with a single solvent or a mixture of solvents with constant composition (isocratic elution) or a mixture of solvents that changes during the run and form a gradient (gradient elution). Preferably, the elution is with a single solvent or a mixture with constant composition. The column is eluted at a flow of between 1 and 100 mL per min. The fractions collected are between 1/10 and 1/100 of the volume of the column. The liquid chromatography is conducted at between 4 and 60° C., preferable at between 15 and 25° C. (ambient temperature).

Preferably, fractionation is conducted after the completion of the two chemical reactions, so that by-products formed during the substitution with the fatty acid and/or the substitution with the sulphate group can be removed simultaneously.

In the examples described below, mixtures enriched in monosulphate carbohydrate fatty acid esters are isolated from the carbohydrate ester mixture prepared by ad random synthesis methods. The conditions of the preparation process are disclosed in detail in WO96/2008 and EP02580226.

The carbohydrate mixtures enriched in MONO can be characterized by the molar ratio of MONO to POLY. Preferably, the molar ratio of MONO to POLY is 10:1, more preferably 20:1, and more preferably 50:1 or and even more preferably 100:1.

In addition to the preparation method of mixtures enriched in MONO according to the present invention, which includes ad random synthesis and purification by liquid chromatography, other preparation methods may be applicable which result in a carbohydrate ester mixture comprising monosulphate carbohydrate fatty acid ester, wherein less than 10 mole % of the carbohydrate ester mixture is substituted with more than one sulphate group.

For example, regio-selective synthesis can be an alternative method to prepare (mixtures enriched in) MONO. Regio-selective preparation can include temporary protection of hydroxyl groups (i.e. protection and de-protection of hydroxyl groups) of the carbohydrate molecule or the use of an enzyme or catalyst. An advantage of regio-selective synthesis is that a single isomer is produced.

The methods for the preparation of mixtures enriched in MONO have the advantage that they are easy, safe and inexpensive, and can be used to obtain a wide variety of carbohydrate ester mixtures enriched in carbohydrates substituted with one sulphate group and at least one fatty acid, wherein less than 10 mole % of the carbohydrate is substituted with more than one sulphate group. It has been shown that adjuvants comprising such mixtures have little or no toxicity and equal or even increased efficacy, relative to known sulpholipid-carbohydrate adjuvants. For this reason, the present invention relates to an adjuvant, comprising a carbohydrate substituted with a sulphate group and at least one fatty acid, wherein less than 10 mole % of the carbohydrate is substituted with more than one sulphate group, and a pharmaceutically acceptable carrier, i.e. an adjuvant comprising a carbohydrate ester mixture comprising a sulpholipid-carbohydrate, which is a carbohydrate substituted with a sulphate group and with at least one fatty acid, wherein less than 10 mol % of the carbohydrate ester mixture is substituted with more than one sulphate group and wherein preferably less than 50 mole % of the carbohydrate ester mixture is a carbohydrate ester without sulphate groups, and a pharmaceutically acceptable carrier.

A pharmaceutically acceptable carrier in this context is any carrier which can be used to deliver or administer the adjuvant and/or the antigenic compound. Preferred pharmaceutically acceptable carriers are a physiological salt solution, a suspension of an insoluble compound in a physiological salt solution or an emulsion of a water-immiscible compound (e.g. an oil) and a physiological salt solution, preferably an oil-in-water emulsion.

A physiological salt solution is known in the art, and is any solution suitable for injection into a living subject, and which solution will not or barely cause by its mere constitution negative effects on the subject into which it is injected. Preferably, a physiological salt solution is sterile. Further preferably, a physiological salt solution has a pH and ionic strength comparable to the ionic strength of the body fluids of the subject into which it is injected (isotonic).

A physiological salt solution may for instance comprise salts, such as Na, K, Li, $NH_4$, Ca and/or Mg-salts of chloride, bromide, phosphate and/or citrate. Preferably, a physiological salt solution is saline, phosphate buffered saline, citrate buffered saline, isotonic ionic solutions, isotonic nonionic solutions and the like. More preferably, the physiological salt solution can be saline or phosphate buffered saline. An example of saline is a sterile solution of 0.9 w/v % of sodium chloride in water.

Alternatively, the pharmaceutically acceptable carrier is a suspension of an insoluble compound in a physiological salt solution. An insoluble compound in this context is for instance an insoluble organic or inorganic compound, which can be used to absorb the monosulphate carbohydrate fatty acid ester. Preferably, the insoluble compound is the known adjuvant alum, which is aluminum hydroxide.

In another preferred embodiment, the pharmaceutically acceptable carrier is an emulsion comprising a water-immiscible compound and a physiological salt solution. Preferably, the type of emulsion is an oil-in-water emulsion. Further preferably, the emulsion is sterile.

The water-immiscible compound is preferably a liquid, more preferably an oil. Suitable oils include one or more selected from the group consisting of squalane, squalene, plant oil and mineral oil. Suitable oils include for example, soybean oil, peanut oil, canola oil, olive oil, safflower oil, corn oil, almond oil, cottonseed oil, ethyl oleate, isopropyl myristate, isopropyl palmitate, mineral oil, myristyl alcohol, octyldodecanol, persic oil, sesam oil, myristyl oleate, cetyl oleate, myristyl palmitate. Other suitable oils include biocompatible oils of saturated, unsaturated, and/or partially hydrogenated fatty acids, silicon-based oil, synthetic oils such as triglycerides composed of saturated and unsaturated chains of $C_{12}$-$C_{24}$ fatty acids, such as for example the glycerol triglyceride ester of oleic acid, terpene, linolene, squalane, squalene, squalamine, and fluorinated oils including perfluoro-compounds known as FC-40, FC-43, FC-72, FC-70, FC-75, perfluorohexane, perflourooctylbromide (also known as perfluorobron), perflourooctyliodine, or any mixture thereof. It is highly preferred if the oil is squalane.

In case of an emulsion, it is generally preferred that the adjuvant comprises an oil at a concentration of between 1-640 g per L, preferably between 2-480 g per L, and more preferably between 4-320 g per L.

Suitable aqueous phases for the emulsion may be any injectable aqueous solution, preferably a physiological salt solution such as for example, saline, phosphate buffered saline, citrate buffered saline, isotonic ionic solutions, isotonic nonionic solutions and the like. The amount of aqueous phase may vary and will usually be between 616 and 996 g per L, such as preferably between 616 and 984 per L or between 680 and 996 per L, more preferably between 680 and 996 per L.

A particularly preferred adjuvant formulation according to the invention comprises a carbohydrate ester mixture comprising a sulpholipid-carbohydrate, wherein less than 10 mole % of the carbohydrate is substituted with more than one sulphate group, such as at a concentration of between 1-640 g per L, preferably between 1-480 g per L, and more preferably between 1-320 g per L.

Excellent results have been achieved with an adjuvant comprising an oil-in-water emulsion wherein the oil is squalane and the water is phosphate buffer saline (PBS).

Optionally, the adjuvant comprises an emulsifier or stabilizer, or a combination of emulsifiers and stabilizers. Any emulsifier or stabilizer suitable for injection purposes can be used, including detergents suitable for this purpose. An example of a suitable emulsifier or stabilizer is Polysorbate 80 (Montannox 80 of Seppic, Paris). If emulsifiers or stabilizers are used, they are typically present in a (total) concentration of 1-640 g per L, preferably 2-480 g per L, and more preferably 4-320 g per L.

Preferably, the adjuvant of the invention is stable and sterile. Preferably, the adjuvant formulation can be sterilized by passing through a sterilizing filter with pore size of 0.05-0.40 μm, preferably 0.15-0.30 μm, preferably around 0.22 μm.

In a preferred embodiment, the adjuvant of the invention comprises between 1 and 80 g/L, preferably between 4 and 64 g/L or between 2 and 40 g/L, more preferably between 4 and 32 g/L and most preferably between 4 and 20 g/L, of a carbohydrate ester mixture enriched in MONO as elsewhere defined, between 1 and 320 g/L, preferably between 2 and and 160 g/L or between 8 and 256 g/L, most preferably between 4 and 80 g/L, of an oil, preferably, squalane and between 1 and 80 g/L, preferably between 4 and 64 g/L or between 2 and 40 g/L, most preferably between 4 and 20 g/L, of an emulsifier or stabilizer, preferably Polysorbate 80, the remainder being aqueous phase, preferably PBS.

Preferably, the adjuvant composition of the invention comprises between 1 and 80 g/L MONO, more preferably between 2 and 40 g/L MONO, even more preferably between 4 and 20 g/L MONO.

The adjuvant of the invention can suitably be used medically, such as to increase the immune response evoked by an antigenic component. Such use is advantageous in applications where the resistance against an antigenic component is to be increased, such as in vaccination.

An antigenic component is any substance which provokes an adaptive immune response in an animal or human. An antigenic component is usually foreign to the body (for example, a bacterium) and, once in the body, elicits a specific immune response by activation of antigen-specific B and T cells. Alternatively, an antigenic component can also be defined as any molecule or molecular fragment that can be recognized by an antigen receptor, such as a B-cell receptor or a T-cell receptor of the adaptive immune system.

Increasing the immune response means for instance that the production of antibodies against the antigenic component, the number of B cells that produce antibodies against the antigenic component, and/or the number of T cells that recognize the antigenic component is increased, relative to the normal situation in which the animal or human is exposed to only the antigenic component. An increased immune response can be determined by for instance determining antibody titers, as is known in the art.

An antigenic component in this context is any compound which evokes an immune response in a human or animal and is also generally referred to as 'immunogen'.

The adjuvant of the invention increases the immune response to the antigenic component in humans and animals. In one preferred embodiment, the adjuvant of the invention is used in humans. In another preferred embodiment, the adjuvant of the invention is used in animals. Preferred animal species are mammals, and include pigs, rats, rabbits, ferrets, cattle, sheep, ponies, monkeys, cats, dogs, and elephants. Preferably, an antigenic component evokes an immune response in at least a human.

It is well-known that an adjuvant itself does not or barely evoke an immune response, but rather an adjuvant increases the immune response to an antigenic component. It is further known that an adjuvant has this effect irrespective of the type of antigenic component to which the immune response is directed. Therefore, the adjuvant of the invention can be used with any antigenic component, to increase the immune response. Antigenic components can be used in both prophylactic and in therapeutic vaccines.

An antigenic component can be among others, but not limited to, an inactivated micro-organism such as killed bacteria, viruses or parasites, components derived from such micro-organisms and components mimicking the relevant components of such micro-organisms prepared by chemical or biotechnological means. An antigenic component can also be an allergen derived from a plant or an animal, or a component mimicking an allergen prepared by chemical or biotechnological means. An antigenic component can also be a component from the host to which an immune response is desired for therapeutic purposes such as the treatment of cancer, immunological and endocrinological diseases.

Examples of the antigenic component of prophylactic vaccines include inactivated influenza virus, inactivated polio virus, inactivated rabies virus, inactivated bacteria, subunits or recombinant DNA products of viruses or bacteria such as hemagglutinin and neuraminidase of influenza virus, tetanus toxoid, diphtheria toxoid, Hepatitis B virus, malaria, papilloma virus, and polysaccharide-protein conjugates with polysaccharide from *Streptococcus pneumoniae, Haemophilus* influenza type b, *Neisseria meningitides*. Preferably, the antigenic component comprises an influenza antigen and/or a malaria antigen.

Examples of the antigenic component of therapeutic allergy vaccines include allergens from grass, mugwort, birch, alder, hazel, and shrubs, house dust, animal, fungi, food and insects.

Examples of the antigenic component of therapeutic vaccines for the treatment of cancer or immunological or endocrinological disorders include (glyco-)proteins or peptide-protein conjugates isolated or mimicking host components such as hormones or factors (e.g. gonadotropin releasing hormone, vascular endothelial growth factor, angiotensin) and cancer cell antigens.

The invention also provides a vaccine, comprising an adjuvant as defined above and an antigenic component. Preferably, the vaccine comprises an oil-in-water emulsion, and further preferably, the vaccine comprises one or several antigenic components as defined above.

For the preparation of a vaccine, a ready-for-use liquid antigenic component may be mixed with a ready-for-use adjuvant formulation according to the present invention at an appropriate volume ratio, such as of 1:100-100:1, preferably 1:50-50:–1, more preferably 1:25-25:1, even more preferably 1:10-10:1. In case of a lyophilized antigenic component, the lyophilized antigenic component may be dissolved in an appropriate volume of a ready-for-use adjuvant formulation according to the present invention, such as between 0.1 and 2 mL for a single dose of vaccine.

A vaccine may comprise per dose 0.01-80 mg, preferably 0.05-80 mg, more preferably 0.05-40 mg, more preferably 0.1-24 mg, more preferably 0.25-20 mg and most preferably 0.25-16 mg of a a carbohydrate ester mixture according to the invention as an adjuvant (i.e. a carbohydrate ester mixture comprising a carbohydrate substituted with a sulphate group and with at least one fatty acid, wherein less than 10 mol % of the carbohydrate is substituted with more than one sulphate group). It may further comprise per dose 1-320 mg, preferably 2-160 mg, and more preferably 4-80 mg of an water-immiscible liquid phase, preferable an oil, and more preferably squalane, and per dose 0.25-80 mg, preferably 0.5-24 mg, and more preferably 1-20 mg (in total) of one or more emulsifiers or stabilizers preferably Polysorbate 80 (Montannox 80 PPI). One dose of vaccine is a single injection volume, and can be for instance between 0.1 and 2.0 mL of injectable liquid. The quantity of antigenic component is a dose of vaccine is highly dependent on the identity of the antigenic component, and can be between 0.1-1000 μg per dose, such as preferably between 1 and 100 μg per dose.

The invention also provides a kit of parts, comprising an adjuvant as described above, and optionally further comprising a preparation comprising an antigenic component, such as a powder, a solution or an emulsion. Also, the kit may comprise syringes, needles, volumetric components and/or injectable liquids, as well as other components known in the art of vaccination to be suitable for inclusion in a kit. It may be desirable to manufacture, transport, and store the adjuvant and the antigen separately or to administer the adjuvant and antigen separately. In such case the adjuvant formulation may be supplied in separate vials or prefilled syringes.

EXAMPLES

The following examples are illustrative, and not limiting, of the invention. The examples demonstrate an unexpectedly high safety of carbohydrate ester mixtures enriched in MONO according to the present invention, in combination with a strongly enhanced immune response in animals that are injected with a vaccine containing the adjuvant of the present invention. The term MONO(s) includes carbohydrate fatty acid sulphate ester(s) with one sulphate group per carbohydrate molecule. In addition, the examples demonstrate an unexpectedly high toxicity of carbohydrate ester mixtures enriched in POLY. The term POLY(s) includes carbohydrate fatty acid sulphate ester(s) with two or more sulphate groups per carbohydrate molecule. MONOs and POLYs are two of the three major constituents of the carbohydrate ester mixtures known in the art, for example CoVaccine HT.

Preparation of Monosulphate Carbohydrate Fatty Acid Ester Derivatives According to the Present Invention:

The monosulphate carbohydrate fatty acid esters according to the present invention are prepared according to the methods known in the art for the preparation of SL-carbohydrates, except that a fractionation step is incorporated to separate the mixture enriched in MONO from the POLY (carbohydrate fatty acid esters substituted with two or more sulphate groups). Preferably, the mixture enriched in MONO is also separated from at least part of the ZERO (carbohydrate fatty acid esters not substituted with a sulphate group).

The synthesis of the monosulphate carbohydrate fatty acid derivatives included a first step of contacting a carbohydrate with a sulphonating agent and a second step of contacting the carbohydrate with a reactive fatty acid acyl compound.

The separation of MONO from ZERO and POLY is conducted either after the first step of the synthesis procedure (i.e. after contacting the carbohydrate with the sulphonating agent) or after the second step of the synthesis procedure (i.e. after reaction of the carbohydrate with a reactive fatty acid acyl compound).

The separation of MONO from ZERO and POLY and (simultaneous) purification of MONO from other by-products can be done by liquid chromatography using silica as the stationary phase and a mixture of organic solvents as the mobile phase.

Example 1: Monosulphate Heptadodecyl Maltose ('M12-MONO')

Maltose monohydrate (0.2 mole; 68.4 g) was dissolved in anhydrous pyridine (200 g) and 0.5 equivalents of $SO_3$.pyridine (0.1 mole; 15.9 g) in warm (50° C.) anhydrous pyridine (300 g) were added. The reaction mixture was stirred for 1 h at room temperature and the inorganic sulphate content was determined by ion-chromatography high performance liquid chromatography (IC-HPLC; Metrohm 821; Metrosep A supp 5-250/4.0 column, 0.1 mM carbonate solution as eluent, detection by conductivity). The inorganic sulphate represents the quantity of sulphonating agent that did not react with the carbohydrate but instead with water present in the starting material or entering the reaction mixture during processing.

Silica (400 g) was dried for 4 hours at 220° C. and suspended in anhydrous pyridine (800 mL) and fed into a dry glass column with inlet and outlet connectors and connectors of PVDF. After settlement of the silica, a sample of 50 mL of maltose monosulphate in anhydrous pyridine was applied. Elution was with 1 L of anhydrous pyridine followed by 1 L of anhydrous N,N-dimethylformamide. Fractions of 50 mL were collected under dry argon or nitrogen and tested on HPTLC (silica plate, developed with butanol:isopropanol:acetic acid:formic acid:water=10:3:26: 6:4, sprayed with 5% sulfuric acid in methanol and heated for 20 min at 100° C.) for the presence of maltose, maltose monosulphate or maltose polysulphate. Maltose eluted with anhydrous pyridine and maltose monosulphate with anhydrous N,N-dimethylformamide.

Fractions containing pure maltose monosulphate were collected, pooled and used for further synthesis. The maltose content was quantified by orcinol/sulphuric acid reagent according Dubois et al (Anal. Chem. 28 pp. 350-355, 1956). Briefly, 50 μL of a sample containing between 0.1 and 1 μg carbohydrate per mL were added with 950 μL orcinol reagent consisting of a solution of 2 g/L orcinol in 70% sulphuric acid. The mixture was mixed vigorously and incubated for 20 min at 100° C. After cooling the absorbance at 550 nm was measured. The carbohydrate concentration was calculated by using standard solutions based on the unsubstituted carbohydrate, maltose monohydrate. Anhydrous pyridine was added and the solution was warmed to 60° C. Eight equivalents of dodecanoylchloride were added and the reaction mixture was kept for 8 h at 70° C. The formation of monosulphate heptadodecyl maltose was monitored by HPTLC (silica plate; developed with n-hexane: diethylether:acetic acid at a volume ratio of 233:100:3.3, sprayed with 5% sulfuric acid in methanol and heated for 20 min at 100° C.).

Example 2; Monosulphate Heptadodecyl Sucrose ('S12')

The SL-sucrose of CoVaccine HT comprising ZERO, MONO and POLY (herein referred to as 'S12') was prepared as described in EP02133969. Sucrose (68.6 g, 0.2 mole) dried for 4 h at 100° C. was dissolved in anhydrous pyridine (188 g; 2.4 mole) and anhydrous N,N-dimethylformamide (388; 5.3 mole). The reaction mixture was kept under dried nitrogen and stirred for 2 hours at 90° C. until a clear solution was obtained. During the synthesis procedure, precautions were taken to avoid contact with water and humid air. After cooling to room temperature, $SO_3$.pyridine (32 g; 0.2 mole; 1.0 equivalent) was added to the reaction mixture under vigorous stirring. After 1 h at room temperature, a sample was taken to measure the inorganic sulphate concentration by IC-HPLC as described in Example 1. Subsequently, the solution was warmed to 60° C. and dodecanoyl chloride (311 g; 1.4 mole; 7.1 equivalent) was added under vigorous stirring. After 4 hours, a sample was collected to determine the degree of esterification by semi-quantitative HPTLC (silica plate; developed with n-hexane: diethylether:acetic acid at a volume ratio of 233:100:3.3, sprayed with 5% sulfuric acid in methanol and heated for 20 min at 100° C.).

An additional portion of dodecanoylchloride (75 g; 0.3 mole; 1.7 equivalent; total of 8.8 equivalents) was added under vigorous stirring. After 4 hours at 70° C., a sample was collected and analysis by semi-quantitative HPTLC revealed that esterification was complete. The solvents were removed at increased temperature (60° C.) and reduced pressure (<20 mBar) at a rotavapor (Büchi). The residue was dissolved in cold methanol (4° C.) at a final concentration of 20 w/w %. After vigorous stirring, the mixture was kept overnight at 4° C. causing a brown viscous lower phase and liquid upper phase. The upper (methanol) phase was collected and extraction of the lower phase was repeated several times with cold methanol (4° C.) with separation of phases overnight at 4° C. The methanol extracts (upper phases) were pooled and clarified by centrifugation for 5 min at 3,000 rpm (1200 g) in 50-mL polypropylene tubes. The supernatants were collected, pooled and the methanol was removed by evaporation at increased temperature (40° C.) and reduced pressure (<20 mBar) at a rotavapor The composition of S12 was determined by semi-quantitative HPTLC as described in Example 1.

TABLE 1

Composition of unfractionated S12, the in-house equivalent of CoVaccine HT, as determined by HPTLC and expressed as mole %. For comparison, the composition of original CoVaccine HT is included.

| Test item | Composition of the flash chromatography fractions of dodecylsucrose | | |
|---|---|---|---|
|  | ZERO | MONO | POLY |
| S12 | 39% | 46% | 15% |
| CoVaccine HT | 32% | 41% | 28% |

Example 3: Monosulphate Tetradodecyl Galactose ('CG12-MONO')

Monosulphate tetradodecyl galactose (herein referred to as 'G12-MONO') was prepared by reaction of galactose in a similar way as described for sucrose in Example 2. Galactose (36.4 g; 0.2 mole), anhydrous pyridine (161 g), anhydrous N,N-dimethylformamide (197 g), $SO_3$.pyridine (31.2 g; 0.2 mole; 1 equivalent) and dodecanoylchloride (268 g; 1.2 mole; 6.2 equivalent) were reacted as described in Example 2. Inorganic sulphate content determined by IC-HPLC was 11% giving an average ratio of 0.89 mole of sulphate per mole of galactose. The ZERO-rich fraction (herein referred to as 'G12-ZERO') contained 100 w/w % ZERO (Table 2). The MONO-rich fraction (herein referred to as 'G12-MONO') contained 25 mole % ZERO and 75 mole % MONO.

TABLE 2

Composition of the three fractions of dodecylgalactose derivatives obtained by liquid chromatography, analyzed by LC-MS and expressed as mole %

|  | Composition of the flash chromatography fractions of dodecylgalactose | | |
|---|---|---|---|
|  | ZERO | MONO | POLY |
| Sulphate content | 0 | 1 | 1 | ≥2 |
| Lipid content | 5 | 4 | 3 | ≤3 |
| Fraction G12-ZERO | 100% | 0% | 0% | 0% |
| Fraction G12-MONO | 25% | 75% | 0% | 0% |

Example 4: Monosulphate Heptadodecyl Maltose ('M12-MONO')

Monosulphate heptadodecylmaltose (herein referred to as 'M12-MONO') was prepared as described in Example 2 for monosulphate heptadodecylsucrose using maltose monohydrate (36.6 g; 0.1 mole), anhydrous pyridine (97 g), anhydrous N,N-dimethylformamide (199 g), $SO_3$.pyridine (31.7 g; 0.2 mole; 2 equivalent) and dodecanoylchloride (224 g; 1.0 mole; 10.4 equivalent). To result in the carbohydrate ester mixture M12 Inorganic sulphate content was 63% from which an average ratio of 0.76 mole of sulphate per mole of maltose was calculated.

The result of the fractionation of M12 is summarized in Table 3. M12-MONO contained 78 mole % monosulphate hepta-dodecylmaltose and 22 mole % monosulphate hexa-dodecylmaltose, which confirms MONO can be obtained with less than the saturated amount of fatty acids.

TABLE 3

Composition of the three fractions of dodecylmaltose derivatives obtained by a one or two flash chromatography, analysed by LC-MS and expressed as mole %.

| | Composition of the flash chromatography fractions of dodecylmattose | | | | | |
|---|---|---|---|---|---|---|
| | ZERO | | MONO | | POLY | |
| Sulphate content | 0 | 0 | 1 | 1 | 2 | 3 |
| Lipid content | 8 | 7 | 7 | 6 | 6 | 5 |
| Fraction M12-ZERO | 61% | 28% | 11% | 0% | 0% | 0% |
| Fraction M12-MONO | 0% | 0% | 78% | 22% | 0% | 0% |
| Fraction M12-POLY | 0% | 0% | 0% | 0% | 87% | 13% |

Example 5: Monosulphate Heptadecyl Maltose ('M10-MONO')

Monosulphate heptadecylmaltose (herein referred to as 'M10-MONO') was prepared as described in Example 3 for monosulphate heptadodecylsucrose. Maltose monohydrate (36.6 g; 0.1 mole), anhydrous pyridine (97 g), anhydrous N,N-dimethylformamide (199 g), S03.pyridine (31.7 g; 0.2 mole; 2 equivalents) and decanoylchloride (154.9 g; 0.8 mole; 9.7 equivalent) were the quantities employed. After sulphonation, inorganic sulphate content was 63% from which an average ratio of 0.76 mole of sulphate per mole of maltose was calculated. Prior to the addition of decanoylchloride, one equivalent of LiCl was added as a solution of anhydrous LiCl in anhydrous pyridine, which resulted in a precipitate of lithium sulphate and complete removal of inorganic sulphate from the reaction mixture.

LC-MS analyses of the fractionated M10 revealed that the MONO fraction contained 98 mole % monosulphate heptadecylmaltose and 2 mole % disulphate hexa-decylmaltose indicating a high degree of purity (Table 4).

TABLE 4

Composition of the three fractions of decylmaltose derivatives obtained by a one or two flash chromatography mole %.

| | Composition of the flash chromatography fractions of decylmaltose | | | | | |
|---|---|---|---|---|---|---|
| | ZERO | | MONO | | POLY | |
| Sulphate content | 0 | 0 | 1 | 1 | 2 | 3 |
| Lipid content | 8 | 7 | 7 | 6 | 6 | 5 |
| Fraction M10-ZERO | 89% | 11% | 0% | 0% | 0% | 0% |
| Fraction M10-MONO | 0% | 0% | 98% | 0% | 2% | 0% |
| Fraction M10-POLY | 0% | 0% | 17% | 0% | 74% | 9% |

Example 6: Adjuvant Effects of the MONOs

The adjuvant effect of the monosulphate carbohydrate fatty acid esters of the present invention was determined in rabbits. For this purpose, Fraction G12-MONO (75 mole % O-monosulphate 0-tetradodecyl galactose plus 25 mole % 0-pentadodecylgalactose) of Example 3, Fraction M12-MONO (78 mole % O-monosulphate 0-heptadodecyl maltose plus 22 mole % O-monosulphate 0-hexadodecyl maltose) of Example 4 and Fraction M10-MONO (98 mole % O-monosulphate 0-heptadecyl maltose plus 2 mole % 0-disulphate 0-hexadecyl maltose) of Example 5 were formulated in a submicron emulsion of squalane-in-water, and compared to the adjuvant effect of S12 (in-house CoVaccine HT analogue), alum (known safe adjuvant) and a control without adjuvant.

For each MONO fraction, the appropriate quantities of squalane (BASF, Germany) and Montannox 80 PPI (Seppic, Paris, France) yielding a formulation that could be passed through a 0.22 µm was determined. Adjuvant formulations were prepared as described in EP1223969 at final concentrations of 16.0 g MONO fraction per L (16 mg/mL). Mixtures of MONO, squalane, Polysorbate 80, ultrapure water and phosphate buffered saline, were passed three times through a high-pressure emulsifier, i.e. Microfluidizer Model Y110 under continuous cooling. The adjuvant formulations obtained were white or bluish emulsions with low viscosity. These formulations were passed through a 0.22 µm PES filter (Corning Inc.) and the filtrates were recovered in sterile bottles. Subsequent handling of the adjuvant formulations was conducted under aseptic conditions. The adjuvant formulations were kept in sealed bottles at 4° C. until use.

Adjuvant M10-MONO was prepared of 4 g of Fraction M10-MONO, 8 g of squalane, 4 g of Montannox 80 PPI, 2 g of ultrapure water and 232 g of phosphate buffered saline (PBS; Fisher Scientific).

Adjuvant G12-MONO was prepared of 4 g of Fraction G12-MONO, 8 g of squalane, 4 g of Montannox 80 PPI, 2 g of ultrapure water and 232 g of PBS.

Adjuvant M12-MONO was prepared of 4 g of Fraction M12-MONO, 16 g of squalane, 4 g of Montannox 80, 2 g of ultrapure water and 224 g of PBS.

Adjuvant S12 (an in-house prepared 'CoVaccine HT' formulation) was prepared of 11 g of unfractionated S12 (Example 2; containing approximately 4.3 g of ZERO, 5.1 g of MONO and 1.7 g of POLY), 44 g of squalane, 11 g of Montannox 80 PPI, 2 g of ultrapure water and 182 g of PBS.

Adjuvant S12 served as a benchmark for strong adjuvants.

Alum (SSI, Denmark) served as a benchmark for safe adjuvants.

Antigen without adjuvant served as negative control.

The composition of the adjuvant formulations tested is summarized in Table 5.

The compositions of the adjuvant formulations were verified by determining the carbohydrate concentrations using orcinol/sulphuric acid as reagent and measuring absorbance at 550 nm as described in Example 1. If required, the concentration of M10-MONO, G12-MONO or M12-MONO in the adjuvant formulations were adjusted to 16.0 g per L.

In addition, the adjuvant formulations were analysed by HPTLC and results are shown in FIG. 1. One µL sample of either adjuvant formulation comprising of an emulsion of SL-carbohydrate, squalane, Polysorbate 80 and PBS was applied on the HPTLC plate. The plate was developed in n-hexane, diethyl ether and acetic acid (at a volume ratio of 233:100:3.3), dried and subsequently developed in triethylamine, 2-isopropanol and heptane (at a volume ratio of 1:3:8). Carbohydrate spots were visualized by spraying with a solution of 5% sulfuric acid in methanol and heating the plate for 30 min at 90° C.

Spots with retention factor of 1.0 (at the top of the plate) represent the ZEROs and is detectable in adjuvant formulation of CoVaccine HT and S12 but not in those of M10-MONO, G12-MONO and M12-MONO. Spots with retention factor of between 0.2 and 0.5 represent the MONOs and is detectable in all adjuvant formulations except the squalane-in-water emulsion lacking SL-carbohydrate, which was used as pharmaceutical carrier and included in this TLC analysis as a control. Spots with retention factor of between 0.0 and 0.1 (bottom of the plate) represent the POLYs and to a lesser extend Polysorbate 80. POLYs are detectable in the adjuvant formulations of CoVaccine HT and S12 and Polysorbate 80 is detectable in all formulations including the squalane-in-water emulsion without SL-carbohydrate.

Semi-quantitative analyses of TLC patterns revealed w/w % of ZERO, MONO and POLY in CoVaccine HT of 32%, 41% and 28%, respectively and in S12 (the CoVaccine HT-like formulation prepared in-house by LiteVax BV) of 39%, 46% and 15%, respectively. Thus as compared to the original CoVaccine HT, S12 adjuvant formulation contained similar quantity of MONO but two-fold lower quantity of POLY The antigen used to demonstrate adjuvant activity of the novel compounds was a recombinant fusion protein of two important malaria antigens known as R0.10C as described by Theisen et al. (Vaccine, 32, pp. 2623-2630, 2014). The antigen has been demonstrated to elicit antibodies that block transmission and asexual growth of a panel of *Plasmodium falciparum* strains of different geographical origin (Theisen et al., Vaccine, 32, pp. 2623-2630, 2014). A stock solution of R0.10C antigen at concentration of 1.33 mg per mL was provided by Radboud UMC, Nijmegen, the Netherlands. The dose was 10 µg of R0.10C protein per injection. The vaccine volume was 0.5 mL per injection. The vaccines of the first immunization consisted of 8 µL of antigen preparation, 242 µL of PBS and 250 µL of adjuvant formulation. As no side effects were observed after the first immunization, it was decided to increase the dose of the experimental adjuvants (Group 3-6) for the second immunization with a factor of two. The dose of M10-MONO, G12-MONO and M12-MONO adjuvant of the first immunization was 4.0 mg and that of the second immunization 8.0 mg. The dose of S12 adjuvant of the first immunization was 11 mg SL-sucrose and that of the second injection 22 mg SL-sucrose. The vaccines of the second immunization consisted of 8 µL of antigen preparation plus 492 µL of adjuvant formulation. The dose of alum (Staten Serum Institute, Denmark) was 110 µg for both the first and second injection.

TABLE 5

Composition of the adjuvant formulations.

| Test item | SL-Carbohydrate derivative type | Squalane g | Montannox 80 PPI g | Ultra-pure water g | PBS (ad 250 g) g |
|---|---|---|---|---|---|
| S12 | S12 | 11.0 | 44.0 | 11.0 | 2.0 | 182 |
| M10-MONO | Fraction M10-MONO | 4.0 | 8.0 | 4.0 | 2.0 | 232 |
| G12-MONO | Fraction G12-MONO | 4.0 | 8.0 | 4.0 | 2.0 | 232 |
| M12-MONO | Fraction M12-MONO | 4.0 | 16.0 | 4.0 | 2.0 | 224 |

The cohort of rabbits was controlled for adequate responsiveness to SL-carbohydrate-based adjuvants. For this purpose, a batch of CoVaccine HT that has proven to generate a rise in body temperature of 1° C. one day after injection in earlier animal studies was used. Six animals of the cohort were injected with 0.5 mL of this reference batch of CoVaccine HT at a dose of 20 mg of carbohydrate (sucrose) fatty acid sulphate ester (corresponding with 6.4 mg of ZERO, 8.2 mg of MONO and 5.6 mg of POLY), 80 g of squalane and 20 g of Polysorbate 80. One day after administration mean body temperature was 40.1 (±0.4) ° C., which is about 0.8° C. above normal values.

Figure 2:
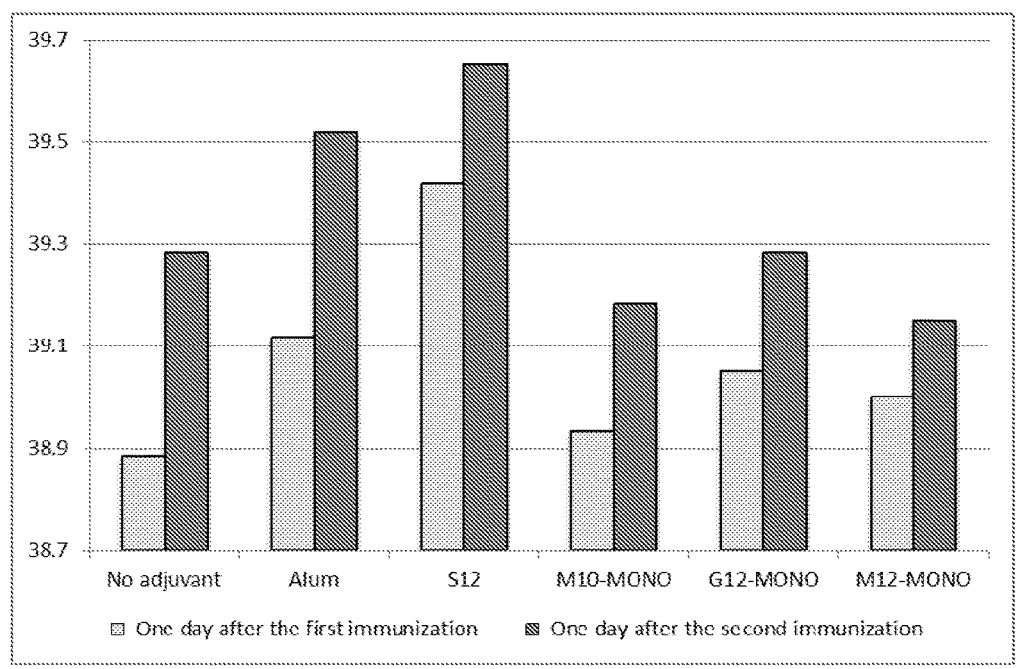
FIG. 2: Mean body temperature (° C.) in rabbits one day after the first (light grey columns) and the second intramuscular immunization (dark grey columns) with recombinant R0.10C antigen plus different adjuvants. The dose of MONO in S12 (a mixture of ZERO, MONO and POLY), M10-MONO, G12-MONO and M12-MONO was 4 mg for the first immunization and 8 mg for the second immunization. The dose of alum of the first and second immunization was 110 μg.

Groups of six female rabbits of 2-3 kg and 20 weeks of age, were immunized intramuscularly on Day 0 in the left (first immunization) and on Day 21 in the right thigh (second immunization). Body temperature was determined at different time intervals before and after treatment. One day after the first and the second injection, some increases in body temperature were noted (see Table 6 and FIG. 2) while at other time intervals normal values were noted (data not shown).

TABLE 6

Body temperature one day after the first and second immunization.

| Group | Test item | Body temperature one day after the first immunization | | Body temperature one day after the second immunization | |
|---|---|---|---|---|---|
| | | Mean | SD | Mean | SD |
| 1 | No adjuvant | 38.9 | 0.2 | 39.3 | 0.4 |
| 2 | Alum | 39.1 | 0.3 | 39.5 | 0.4 |
| 3 | S12 | 39.4$^a$ | 0.3 | 39.7$^a$ | 0.5 |
| 4 | M10-MONO | 38.9 | 0.4 | 39.2 | 0.5 |
| 5 | G12-MONO | 39.1 | 0.5 | 39.3 | 0.2 |
| 6 | M12-MONO | 39.0 | 0.5 | 39.2 | 0.4 |

$^a$Significantly higher than the other four adjuvant groups taken together.

None of the three MONO fractions (Group 4, 5 and 6) at doses of 4 and 8 mg induced significant increase in mean body temperature. The S12 (CoVaccine HT-like) at doses of 11 (containing 4.3 mg of ZERO, 5.1 mg of MONO and 1.7 mg of POLY) and 22 mg (containing 8.6 mg of ZERO, 10.2 mg of MONO and 3.4 mg of POLY) gave a rise in body temperature one day after the first and second immunization of about 0.5° C., which was significantly higher than the overall reaction in the other groups (Group 1, 2, 4, 5 and 6). Body temperature returned to normal values one day later (data not shown). The increase in body temperature with S12 was about half of that noted with CoVaccine HT, which is considered to be the consequence of the two-fold lower dose of POLY in S12 as compared to CoVaccine HT.

One week after the second immunization, animals were euthanized and local reactions were scored at both sites of injection as described in Hilgers (Methods Mol. Biol. 626 pp. 251-9, 2010). The score of each injection site is the product of the size (length×width×depth in mm) and nature of the local reaction with the following arbitrary scores: 1 for oedema, discoloration, and loss of muscular structure, 3 for fibrosis, granuloma and connective tissue, 9 for necrosis and pus; 12 for vaccine residue.

None of the animals exhibited moderate or severe local reactions. In a few animals mild adverse event were noted. Except in one animal (in Group 5), the dimensions of the local reactions were between 0 and a few millimeters and the arbitrary scores of local reactions were mostly 0 and sometimes 1 (indicating discoloration and loss of muscular structure). From all animals tested, only one animal had a score higher than 1, and all others had an overall score of 1 or less. Local reactions were unexpectedly low and the detection limit of the scoring system anticipated was not suitable to discriminate between these low scores. Therefore, the number of animals per group with a detectable local reaction, albeit minimal, was reported (Table 7).

TABLE 7

Local reactions four weeks after the first
and one week of the second immunization.

| Group | Test item code | Number of animals demonstrating a detectable adverse local reaction four weeks after the first immunization[a] | Number of animals demonstrating a detectable adverse local reaction one week after the second immunization[a] |
|---|---|---|---|
| 1 | No adjuvant | 0/6 | 0/6 |
| 2 | Alum | 0/6 | 1/6 (redness) |
| 3 | S12 | 1/6 (redness) | 2/6 (redness/swelling) |
| 4 | M10-MONO | 0/6 | 0/6 |
| 5 | G12-MONO | 1/6 (discoloration, loss muscular structure) | 1/6 (granuloma) |
| 6 | M12-MONO | 0/6 | 0/6 |

[a]The local reactions represent the number of animals out of the 6 animals per group exhibiting a significant albeit minimal local effect.

The local reactions of the MONOs were significantly lower than those observed previously with CoVaccine HT or similar products.

Blood samples were collected before the first immunization (Day 0), three weeks after the first immunization (Day 21) and one week after the second immunization (Day 28). Antibody titres were measured by ELISA using the antigen R0.10C used for immunization for coating the ELISA plates as described by Theisen et al. (Vaccine, 32, pp. 2623-2630, 2014). Arithmetic mean antibody titres (AMTs) and standard deviations (SDs) are given in Table 8.

TABLE 8

Antibody response three weeks after the first and one
week of the second immunization by ELISA using R0-10C as antigen[a].

| | | Antibody response three weeks after the first immunization | | Antibody response one week after the second immunization | |
|---|---|---|---|---|---|
| Group | Test item | AMT | SD | AMT | SD |
| 1 | No adjuvant | 46.5 | 22.3 | 1,763.3 | 2206.5 |
| 2 | Alum | 48.7 | 39.7 | 1,923.8 | 1223.6 |
| 3 | S12 | 1,992.6 | 1,797.7 | 106,070.7 | 70,664.9 |
| 4 | M10-MONO | 1,271.3 | 1,159.8 | 105,679.8 | 58,322.7 |
| 5 | G12-MONO | 479.8 | 231.5 | 60,490.8 | 26,248.5 |
| 6 | M12-MONO | 258.7 | 202.5 | 35,888.8 | 25,921.5 |

[a]AMT ± SD before the first immunization at Day 0 were 25.6 ± 9.3.

Geometric mean antibody titres (GMTs) and standard deviations (SDs) three weeks after the first immunization (Day 21) and one week after the second immunization Day 28) and antilogs ($10^{GMT}$) are represented in Table 9.

TABLE 9

Antibody response three weeks after the first and one week of
the second immunization by ELISA using R0-10C as antigen[a].

| | | $^{10}$Log antibody response three weeks after the first immunization | | | $^{10}$Log antibody response one week after the second immunization | | |
|---|---|---|---|---|---|---|---|
| Group | Test item | GMT | SD | antilog | GMT | SD | antilog |
| 1 | No adjuvant | 1.6 | 0.2 | 41.9 | 2.9 | 0.6 | 804.5 |
| 2 | Alum | 1.6 | 0.2 | 40.8 | 3.2 | 0.3 | 1,553.4 |
| 3 | S12 | 3.1 | 0.4 | 1,325.6 | 5.0 | 0.2 | 91,061.2 |
| 4 | M10-MONO | 2.9 | 0.4 | 882.8 | 4.9 | 0.3 | 88,308.0 |
| 5 | G12-MONO | 2.6 | 0.2 | 428.2 | 4.7 | 0.2 | 55,964.3 |
| 6 | M12-MONO | 2.3 | 0.4 | 183.1 | 4.4 | 0.4 | 26,822.5 |

[a]GMT ± SD before the first immunization at Day 0 was 1.4 ± 0.2 and antilog was 23.2

Antibody titers against gametocyte extract of *Plasmodium falciparum* were measured as described in Theisen et al. (Vaccine 32, pp. 2623-2030, 2014). Geometric mean antibody titres (GMTs) and standard deviations (SDs) three weeks after the first immunization (Day 21) and one week after the second immunization (Day 28) and antilog values ($10^{GMT}$) are represented in Table 10.

TABLE 10

Antibody response three weeks after the first and one
week of the second immunization by ELISA using gametocyte extract
of *Plasmodium falciparum* as antigen[a].

| | | $^{10}$Log antibody response three weeks after the first immunization | | | $^{10}$Log antibody response one week after the second immunization | | |
|---|---|---|---|---|---|---|---|
| Group | Test item | GMT | SD | antilog | GMT | SD | antilog |
| 1 | No adjuvant | 1.5 | 0.1 | 31.7 | 1.8 | 0.2 | 57.3 |
| 2 | Alum | 1.6 | 0.2 | 39.5 | 2.0 | 0.1 | 102.2 |
| 3 | S12 | 1.9 | 0.2 | 72.3 | 3.8 | 0.1 | 6,511.3 |
| 4 | M10-MONO | 2.2 | 0.2 | 152.9 | 3.9 | 0.2 | 7,976.9 |
| 5 | G12-MONO | 1.8 | 0.3 | 59.4 | 3.7 | 0.3 | 4,971.6 |
| 6 | M12-MONO | 1.7 | 0.1 | 51.5 | 2.8 | 0.2 | 586.3 |

[a]GMT ± SD before the first immunization at Day 0 was 1.5 ± 0.1 and antilog was 32.5.

Antibody titers were measured also against asexual stage measured by ELISA using schizont extract of *Plasmodium falciparum* as antigen as described by Theisen et al (Vaccine 32, pp. 2623-2030, 2014). Geometric mean antibody titres (GMTs), standard deviations (SDs) and antilog values ($10^{GMT}$) three weeks after the first immunization (Day 21) and one week after the second immunization (Day 28) are represented in Table 11.

TABLE 11

Antibody response three weeks after the first and one
week of the second immunization by ELISA using schizont extract
of *Plasmodium falciparum* as antigen[a].

| | | $^{10}$Log antibody response three weeks after the first immunization | | | $^{10}$Log antibody response one week after the second immunization | | |
|---|---|---|---|---|---|---|---|
| Group | Test item | GMT | SD | antilog | GMT | SD | antilog |
| 1 | No adjuvant | 1.6 | 0.1 | 43.5 | 1.7 | 0.2 | 54.1 |
| 2 | Alum | 1.8 | 0.2 | 67.1 | 2.0 | 0.3 | 108.2 |
| 3 | S12 | NT | NT | NT | 2.8 | 0.3 | 671.7 |
| 4 | M10-MONO | NT | NT | NT | 3.0 | 0.2 | 991.3 |
| 5 | G12-MONO | NT | NT | NT | 2.8 | 0.3 | 671.6 |
| 6 | M12-MONO | NT | NT | NT | 2.5 | 0.4 | 297.5 |

[a]GMT (SD) before the first immunization at Day 0 were not determined.

Figure 3:
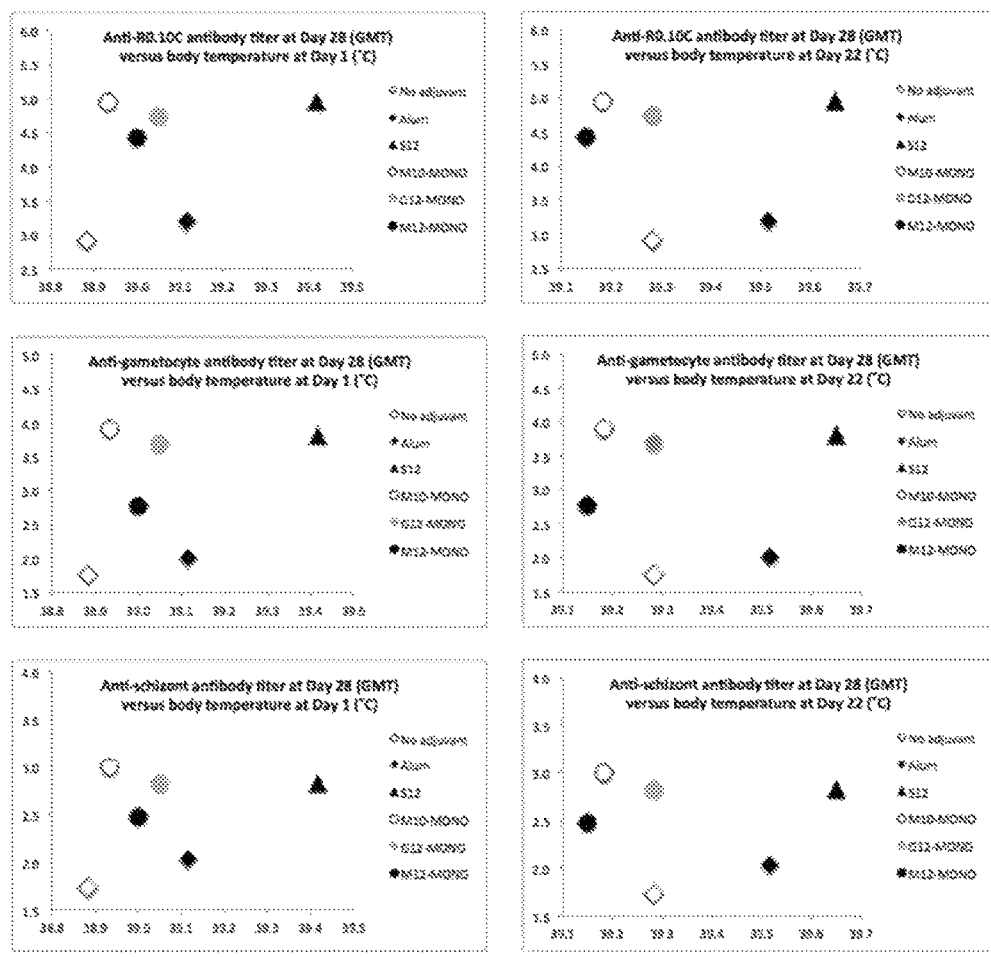
FIG. 3: Efficacy/toxicity-ratio in rabbits of antigen alone (open diamonds), alum (grey diamonds), S12 (black triangles), M10-MONO (open circles), G12-MONO (grey circles) and M12-MONO (black circles). Efficacy (Y-axis) is expressed as the geometric mean ELISA antibody titers ($^{10}$log values) against recombinant R0.10C antigen (upper panels), gametocyte extract of *Plasmodium falciparum* (middle panels) and schizont extract of *P. falciparum* (lower panels) one week after the second immunization (Day 28). Toxicity (X-axis) is expressed as the body temperature (° C.) one day after the first immunization (Day 1, left panels) and one day after the second immunization (Day 22, right panels).
Figure 4A:
FIG. 4a: Animal 821; Group 4; Adjuvant G10-MONO; Toxicity score=0.10; antilog=1
Figure 4B:
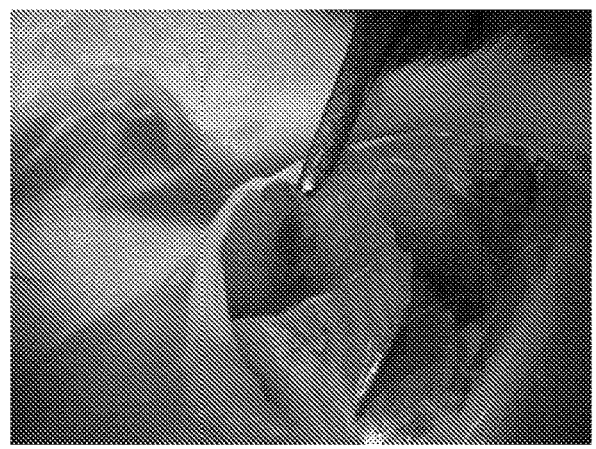
FIG. 4b: Animal 825; Group 5; Adjuvant G10-POLY; Toxicity score=5.51; antilog=324,000
Figure 4C:
FIG. 4c: Animal 832; Group 7; Adjuvant M10-POLY; Toxicity score=5.29; antilog=194,400
Figure 4D:
FIG. 4d: Animal 834; Group 5; Adjuvant G10-POLY; Toxicity score 4.99; antilog 97,200
Figure 4E:
FIG. 4e: Animal 839; Group 5; Adjuvant G10-POLY; Toxicity-score=4.91; antilog=81,000
Figure 4F:
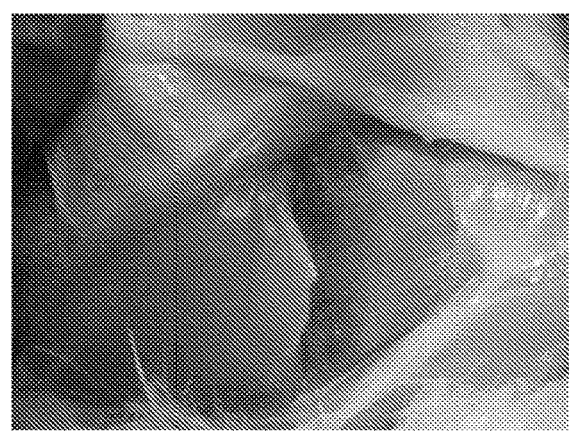
FIG. 4f: Animal 841; Group 5; Adjuvant G10-POLY; Toxicity score=4.29; antilog=19,440
Figure 4G:
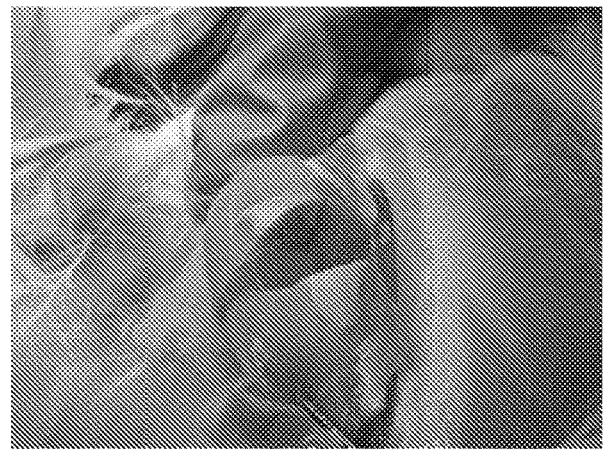
FIG. 4g: Animal 843; Group 5; Adjuvant G10-POLY; Toxicity score=4.74; antilog=54,432
Figure 4H:
FIG. 4h: Animal 845; Group 7; Adjuvant M10-POLY; Toxicity score=6.11; antilog=1,296,000
Figure 4I:
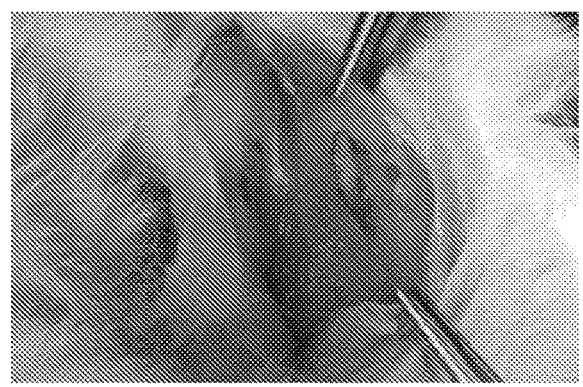
FIG. 4i: Animal 850; Group 7; Adjuvant M10-POLY; Toxicity score=5.08; antilog=121,500

Taken together these in vivo data and as illustrated in FIG. 3, the E/T-ratio of the MONO fractions of the present invention is superior over that of the known S12, which is a mixture of ZERO, MONO and POLY. The MONO fractions of the present invention are equally or slightly more effective than S12 and significantly more effective than alum. In addition, the MONO fractions of the present invention are equally or slightly less toxic than alum and significantly less toxic than S12. In other words, adjuvant formulations enriched in MONO combine the efficacy of CoVaccine HT (the mixture of ZERO, MONO and POLY and benchmark for strong adjuvants) with the safety of alum (the benchmark for safe adjuvants). Adjuvants with such E/T-ratio are candidates for widespread applications in existing and novel immunological products including vaccines.

The dose of MONO in the S12 adjuvant formulation is similar to those of M10-MONO, G12-MONO and M12-MONO. Another conclusion from the data is that the E/T-ratio of MONO is significantly higher than that of ZERO or POLY or both.

Example 7: Optimization of the Purification of Monosulphate Heptadecyl Maltose ('M10-MONO') by Liquid Chromatography To further improve the method for the isolation of a MONO fraction from mixtures of ZERO, MONO and POLY, liquid chromatography was conducted with various combinations of stationary and mobile phases. Excellent results in terms of purity and yield were obtained with dried silica high-purity grade, pore size 60 Å, 230-400 mesh particle size, 40-63 μm (Fluka, catalogue number 60737) and an eluent consisting of 12 v/v % triethylamine (Sigma-Aldrich, catalogue number 90340). 12 v/v % 2-isopropanol (Sigma-Aldrich, catalogue number 24137; Ph. Eur) and 76 v/v % heptane (Sigma-Aldrich, catalogue number 32287; Ph. Eur). Twenty g of M10 in 60 mL eluent were applied to a column prepared from 260 g silica (dried in a vacuum oven for at least 3 h at 160° C. and <100 mBar) in about 500 mL of eluent. The column was eluted at a flow of about 3 L per h and fractions of 50 mL were collected. Each fraction was analyzed by HPTLC (Sigma-Aldrich Uniplate Catalogue number Z26531-4) with 20 v/v % isopropanol in heptane as eluent. M10-ZERO was eluted at between 400 and 600 mL. M10-MONO was eluted at between 800 and 3200 mL. POLY remained on the column and could be eluted with 100% 2-isopropanol. A single liquid chromatography run resulted in a recovery of >90% M10-MONO with <2% ZERO and <2% POLY as determined by semi-quantitative HPTLC analysis.

Example 8: Comparison of MONO and POLY

Preparation of MONOs and POLYs

Galactose fatty acid sulphate ester, maltose fatty acid sulphate ester and maltotriose fatty acid sulphate ester were synthesized by contacting D-(+)-galactose, D-(+)-maltose and maltotriose with SO3.pyridine and decanoylchloride (all obtained from Sigma-Aldrich) as described in Example 1.

The MONOs galactose tetradecanoic acid monosulphate ester hereinabove referred to as monosulphate tetradecyl galactose (G10-MONO), maltose heptadecanoic acid monosulphate ester hereinabove referred to as monosulphate heptadecyl maltose ('M10-MONO') and maltotriose nona-/decadecanoic acid monosulphate ester (herein referred to as 'T10-MONO') and the POLYs galactose decanoic acid polysulphate ester (herein referred to as 'G10-POLY'), maltose decanoic acid polysulphate ester (herein referred to as 'M10-POLY') and maltotriose decanoic acid polysulphate ester (herein referred to as 'T10-POLY') were isolated from galactose fatty acid sulphate ester, maltose fatty acid sulphate ester and maltotriose fatty acid sulphate ester, respectively by preparative liquid chromatography using dry silica as stationary phase. The MONOs were eluted with a mixture of n-heptane, isopropanol and triethylamine (76:12:12 volume %) and the POLYs with a mixture of isopropanol, triethylamine, methanol and ultrapure water (e.g. 50:20:20:10 volume %). Fractions were analyzed by TLC with silica plates and n-heptane, isopropanol and triethylamine (76:12:12 vol. %) as eluent. Spots were visualized by spraying with 5 v/v % sulphuric acid in methanol and heating for 10-20 min at 100° C. Fractions with pure MONOs or POLYs were pooled and evaporated to dryness.

Sterile, ready-for-use adjuvant formulations of the type oil-in-water were prepared by mixing of MONO or POLY, Tween 80, squalane and phosphate buffered saline (PBS), passing the mixtures three times though a high-pressure emulsifier, passing the submicron emulsions through a 0.2 μm filter and recovering the emulsions in sterile containers. The concentrations of MONO or POLY, Tween 80 and squalane were 40 g/L.

Aqueous formulations of MONOs and POLYs in PBS were prepared by adding 1 g of Polysorbate 80 per g of MONO or POLY.

Stability of the Submicron Emulsions Containing MONOs and POLYs

After two weeks at 4° C. or room temperature, emulsions with one of the POLYs but not without POLY or with one of the MONOs exhibited separation of phases. This shows that POLYs but not MONOs have a detrimental effect of the physical stability of the emulsions.

In Vitro Hemolytic Activity of MONOs and POLYs

The hemolytic activity of MONOs and POLYs was determined by mixing serial dilutions of aqueous formulations of either compound in PBS with 1 v/v % sheep red blood cells in a 96-well V-shape microtiter plates (Greiner). After 1 h of incubation at ambient temperature, the concentration of the compound giving 50% hemolysis was determined (Table 12). The hemolytic activity of the MONOs G10-MONO, M10-MONO and T10-MONO was 100 to >3000-fold lower than that of the POLYs G10-POLY, M10-POLY and T10-POLY.

TABLE 12

Hemolytic activity of various MONOs and POLYs.

| Entry | Compound | Concentration giving 50% hemolysis (mg/mL) |
|---|---|---|
| A | G10-MONO | >10 |
| B | G10-POLY | 0.003 |
| C | M10-MONO | >10 |
| D | M10-POLY | 0.3 |
| E | T10-MONO | >10 |
| F | T10-POLY | 0.1 |

In Vivo Effects of MONOs and POLYs

Groups of six rabbits were immunized intramuscularly at Day 0 (pre-immune) and Day 21 with H5N1 grown on Madin Canine Kidney Cells (kindly provided by Medigen Vaccine Corp., Taiwan) at a dose of 15 μg HA with or without adjuvant. Immune response (Table 13 and 14a-c), body temperature (Table 15), body weight gain (Table 16) and local reaction (Table 17 and FIG. 4 a-i) were determined at predefined time intervals in individual animals. In vivo and ex vivo analyses were conducted as single blind tests and treatments were disclosed after the completion thereof.
Effect of MONOs and POLYs on the Immune Response Blood samples of the 7 groups of 6 animals were collected at Day 0, 21 and 28. Antibody titers in individual serum samples of Day 21 and Day 28 and in 6 pools of 7 serum samples of Day 0 were determined.

The hemagglutination inhibition (HI) antibody titers against H5N1 were measured as described by World Health Organization in Laboratory Procedures 'Serological detection of avian influenza A(H7N9) virus infections by modified horse red blood cells hemagglutination-inhibition assay' (2013) with some modifications. Briefly, 100 μL of serum samples pre-treated for 30 min at 56° C. were added with 400 μL of cold PBS containing 0.5 w/v % of protease free bovine serum albumin fraction V ('PBS/BSA'; Sigma) and 50 μL of packed horse red blood cells. After 30 min at cold and centrifugation, 100 μL of the supernatants were recovered, added with 100 μL of a solution of receptor destroying enzyme (cholera filtrate; Sigma) in PBS/BSA and kept overnight at 37° C. Subsequently, the pre-treated serum samples were kept for 30 min at 56° C. to destroy the enzyme. Fifty μL of these serum samples pre-diluted 1/10, were serially diluted two-fold in PBS/BSA. 50 μL of a H5N1 suspension in PBS/BSA containing 8 hemagglutination units were added and kept for 30 min at room temperature. Subsequently, 50 μL of a suspension of 0.75% of packed horse red blood cells in PBS/BSA and agglutination inhibition was determined after 60 min.

The pools of pre-immune serum gave HI titer of 13 (Table 13). After the first immunization without adjuvant, the titer was 34 and with adjuvant between 57 and 113. The factor of increase was between 2 and 3. After the second immunization without adjuvant the titer increased to 135 and with adjuvant to between 359 and 1208. The factor of increase varied from 3 to 9.

TABLE 13

HI antibody response to H5N1 after the first and second immunization with H5N1 with different adjuvants[a].

| | | 3 weeks post immunization 1 | | | | 1 weeks post immunization 2 | | | |
|---|---|---|---|---|---|---|---|---|---|
| Group | Adjuvant | GMT | SD | Antilog | Factor of Increase | GMT | SD | Antilog | Factor of Increase |
| 1 | PBS | 5.1 | 0.4 | 34 | | 7.1 | 0.8 | 135 | |
| 2 | G10-MONO | 6.2 | 0.2 | 76 | 2 | 8.5 | 1.0 | 359 | 3 |
| 3 | G10-POLY | 5.8 | 0.9 | 57 | 2 | 8.6 | 0.4 | 381 | 3 |
| 4 | M10-MONO | 6.6 | 1.2 | 95 | 3 | 9.3 | 0.7 | 640 | 5 |
| 5 | M10-POLY | 6.8 | 0.8 | 113 | 3 | 10.2 | 0.7 | 1,208 | 9 |

[a]GMT ± SD before the first immunization at Day 0 was 3.7 ± 0.3 and antilog was 13.

Homologous antibody titers to H5N1 (designated as 'H5N1' Medigen Vaccine Corp., Taiwan) and heterologous (cross-reactive) antibody titers to A/New Jersey H1N1 (designated as 'H1N1'; commercial batch kindly provided by Solvay-Pharmaceuticals, Weesp, the Netherlands) and A/Panama 2007/1999 H3N2 (designated as 'H3N2'; commercial batch kindly provided by Solvay-Pharmaceuticals, Weesp, the Netherlands) were determined by ELISA with H5N1, H1N12 and H3N2 as coating antigen.

Test conditions were verified in pilot studies. ELISA plates were coated with 2 μg of antigen per mL coatings buffer (carbonate buffer; 0.1 M; pH=9.6). After washing, the plates were blocked with 2 w/v % bovine serum albumin (Sigma-Aldrich) in phosphate buffered saline. Serum samples were pre-diluted and serially diluted in 1 w/v % bovine serum albumin in phosphate buffered saline. Goat anti-rabbit IgG-HRPO conjugate (goat anti-rabbit IgG (H&L), F(ab)2 Fragment—affinity purified, horse radish peroxidase conjugate, 1 mg/mL; Novex, US) was diluted 1/10,000 in 1 w/v % bovine serum albumin in phosphate buffered saline. A ready-for-use solution of 3,3',5,5'-tetramethylbenzidine (Sigma-Aldrich) was used as substrate. The enzymatic reaction was stopped after 20 min at room temperature with one volume of 1 M sulphuric acid. Titers were calculated from the regression coefficient of the linear part of the plot of serum concentration versus extinction value and expressed as the log values of the serum concentration yielding an optical density of 1.0. No significant responses (log value <1) were noted in absence of coating antigen. For each group, geometric mean titer (GMT), standard deviation (SD) and antilog value were calculated. Factors of increase were calculated by dividing the antilog value of the adjuvant group by that of the control (PBS) group. ELISA titers to H5N1, H1N1 and H3N2 at Day 0 (pre-immune) were low and considered background of the test system.

Anti-H5N1 antibody titers after the first and second immunization without adjuvant were 11,676 and 488,299, respectively and the adjuvants gave up to 5-fold increases (Table 14a).

Anti-H1N1 antibody titer after two immunizations without adjuvant was 7,911 and the adjuvants gave up to 3-fold increases (Table 14b).

Anti-H3N2 antibody titers after the first and second immunization were 444 and 776, respectively and the adjuvants gave up to 6-fold increases in responses (Table 14c).

In comparison to G10-POLY, G10-MONO gave higher ELISA antibody responses to H5N1, H3N2 and H1N1. In comparison to M10-POLY, M10-MONO gave higher responses to H3N2 and H1N1 but similar responses to H5N1. Thus, MONO displays at least equal and often better activity than the corresponding POLY.

Surprisingly, immunization with G10-POLY and M10-POLY results in low titers to H3N2 and H1N1, sometimes even lower than immunization without adjuvant. An explanation is that antigenic moieties of the immunogen are destroyed by G10-POLY and M10-POLY. Such detrimental effect of POLYs is a serious drawback, because it has a negative influence on quality and stability of the vaccine. As these dramatic effects occur already within a few days after mixing of antigen and adjuvant and keeping the mixtures at low temperature (4° C.), the presence of POLY in a vaccine preparation should be avoided as much as possible.

As H5N1 used for immunization and H3N2 and H1N1 used for detection were grown on different substrates and purified, anti-H3N2 and anti-H1N1 antibodies recognize cross-reactive, viral antigens. The detrimental effects on cross-reactive antigenic moieties render POLYs unsuitable as adjuvants for a universal influenza vaccine based on cross-reactive antigens.

TABLE 14a

Effect of different adjuvants on ELISA antibody response to H5N1 (the immunogen) after immunization with H5N1[a].

| Group | Adjuvant | GMT | SD | Antilog | Factor of increase |
|---|---|---|---|---|---|
| Day 21 (3 weeks post immunization 1) | | | | | |
| 1 | PBS | 4.07 | 0.30 | 11,676 | |
| 2 | G10-MONO | 4.51 | 0.47 | 32,580 | 3 |
| 3 | G10-POLY | 4.16 | 0.27 | 14,576 | 1 |
| 4 | M10-MONO | 4.63 | 0.20 | 42,674 | 4 |
| 5 | M10-POLY | 4.77 | 0.25 | 59,068 | 5 |
| Day 28 (1 week post immunization 2) | | | | | |
| 1 | PBS | 5.69 | 0.20 | 488,299 | |
| 2 | G10-MONO | 6.14 | 0.19 | 1,377,014 | 3 |
| 3 | G10-POLY | 5.88 | 0.15 | 764,064 | 2 |
| 4 | M10-MONO | 6.37 | 0.06 | 2,364,597 | 5 |
| 5 | M10-POLY | 6.42 | 0.42 | 2,635,128 | 5 |

[a]GMT ± SD before the first immunization at Day 0 was 1.23 ± 0.38 and antilog was 17.

TABLE 14b

Effect of different adjuvants on ELISA antibody response to H1N1 after immunization with H5N1 in rabbits[a].

| Group | Adjuvant | GMT | SD | Antilog | Factor of increase |
|---|---|---|---|---|---|
| Day 28 (1 week post immunization 2) | | | | | |
| 1 | PBS | 3.90 | 0.31 | 7,911 | |
| 2 | G10-MONO | 4.32 | 0.37 | 21,117 | 3 |
| 3 | G10-POLY | 3.63 | 0.43 | 4,278 | <1 |
| 4 | M10-MONO | 4.35 | 0.42 | 22,312 | 3 |
| 5 | M10-POLY | 4.22 | 0.21 | 16,732 | 2 |

[a]GMT ± SD before the first immunization at Day 0 was 0.29 ± 0.23 and antilog was 2.

TABLE 14c

Effect of different adjuvants on ELISA antibody response to H3N2 after immunization with H5N1 in rabbits[a].

| Group | Adjuvant | GMT | SD | Antilog | Factor of increase |
|---|---|---|---|---|---|
| Day 21 (3 weeks post immunization 1) | | | | | |
| 1 | PBS | 2.65 | 0.50 | 444 | |
| 2 | G10-MONO | 3.10 | 0.43 | 1,245 | 3 |
| 3 | G10-POLY | 1.91 | 0.39 | 81 | <1 |
| 4 | M10-MONO | 3.12 | 0.33 | 1,329 | 3 |
| 5 | M10-POLY | 2.74 | 0.55 | 550 | 1 |
| Day 28 (1 week post immunization 2) | | | | | |
| 1 | PBS | 2.89 | 0.44 | 776 | |
| 2 | G10-MONO | 3.31 | 0.50 | 2,050 | 3 |
| 3 | G10-POLY | 1.73 | 0.53 | 54 | <1 |
| 4 | M10-MONO | 3.67 | 0.65 | 4,711 | 6 |
| 5 | M10-POLY | 2.80 | 0.29 | 634 | <1 |

[a]GMT ± SD before the first immunization at Day 0 was 0.52 ± 0.33 and antilog was 3.

Effect of MONOs and POLYs on Body Temperature

Body temperature of individual rabbits were measured at various daily intervals before and after immunization. Mean±SD increase in body temperature one and two days after the first immunization are represented in Table 15. In comparison to the corresponding POLY counterpart, G10-MONO and M10-MONO gave lower increases in body temperature.

TABLE 15

Increase in body temperature one and two days after the first immunization.

| | | One day post immunization 1 (° C.) | | Two days post immunization 1 (° C.) | |
|---|---|---|---|---|---|
| Group | Adjuvant | mean | SD | mean | SD |
| 1 | PBS | 0.1 | 0.2 | 0.0 | 0.2 |
| 2 | G10-MONO | 0.3 | 0.4 | 0.0 | 0.2 |
| 3 | G10-POLY | 0.4 | 0.4 | 0.0 | 0.5 |
| 4 | M10-MONO | 0.5 | 0.4 | 0.1 | 0.2 |
| 5 | M10-POLY | 0.7 | 0.4 | 0.5 | 0.3 |

Effect of MONOs and POLYs on Body Weight Gain

Body weight gain of individual rabbits was monitored and mean±SD increase in two weeks after the first immunization is represented in Table 16. The experimental animals were young and still expected to grow, so that lower body weight gain reflects growth inhibition as an undesired side-effect of the treatment. It was found that under similar conditions of housing and feeding the animals, G10-POLY gave significantly lower body weight gain than G10-MONO.

TABLE 16

Increase in body weight after the first immunization.

| | | Starting weight at Day 0 (g) | | Body weight gain one week post immunization 1 (g) | | Body weight gain two weeks post immunization 1 (g) | |
|---|---|---|---|---|---|---|---|
| Group | Adjuvant | mean | SD | mean | SD | mean | SD |
| 1 | PBS | 3,332 | 316 | 41 | 76 | 80 | 50 |
| 2 | G10-MONO | 3,347 | 271 | 75 | 77 | 138 | 110 |
| 3 | G10-POLY | 3,292 | 217 | 17 | 25 | 38 | 21 |
| 4 | M10-MONO | 3,387 | 295 | 35 | 51 | 49 | 73 |
| 5 | M10-POLY | 3,292 | 242 | 38 | 111 | 53 | 40 |

Effect of MONOs and POLYs on Local Reactions after Immunization

Local reactions were analyzed at Day 28 and geometric mean score (GMS)±SD and antilog value of each group are represented in Table 17. One week after the second immunization, G10-POLY and M10-POLY gave scores of 12,261 and 2,364 respectively, while G10-MONO and M10-MONO gave significantly lower scores of 51 and 22, respectively. The dimensions of the local reactions to the POLYs were up to 2 cm in diameter and showed granuloma and necrosis as illustrated in FIG. 4*b-i*).

TABLE 17

Local reaction at the site of injection after the first and second immunization.

| | | Reactogenicity 4 weeks post immunization 1 | | | Reactogenicity 1 week post immunization 2 | | |
|---|---|---|---|---|---|---|---|
| Group | Adjuvant | GMS | SD | antilog | GMS | SD | antilog |
| 1 | PBS | 0.10 | 0.00 | 1 | 0.10 | 0.00 | 1 |
| 2 | G10-MONO | 0.21 | 0.28 | 2 | 1.70 | 1.40 | 51 |

TABLE 17-continued

Local reaction at the site of injection
after the first and second immunization.

| Group | Adjuvant | Reactogenicity 4 weeks post immunization 1 | | | Reactogenicity 1 week post immunization 2 | | |
|---|---|---|---|---|---|---|---|
| | | GMS | SD | antilog | GMS | SD | antilog |
| 3 | G10-POLY | 0.75 | 1.60 | 6 | 4.09 | 1.99 | 12.261 |
| 4 | M10-MONO | 1.26 | 1.32 | 18 | 1.34 | 1.37 | 22 |
| 5 | M10-POLY | 1.73 | 1.78 | 53 | 3.37 | 2.67 | 2.364 |

These adverse effects of the POLYs but not the MONOs illustrate unambiguously the present invention. A striking example is G10-MONO versus G10-POLY. As compared to G10-POLY, G10-MONO reveals 40-fold higher anti-H3N2 and 5-fold higher anti-H1N1 antibody response one week after the second immunization, 4-fold higher body weight gain in the two weeks after the first immunization, 2-fold lower increase in body temperature after the first immunization and 240-fold lower local reaction score one week after the second immunization.

Combining the data on efficacy for example the anti-H3N2 antibody titer and toxicity for example local reaction score one week after the second immunization reveals an efficacy/toxicity(E/T)-ratio of G10-MONO of 2050/51=40 and of G10-POLY of 54/12,261=0.0044. This means that the E/T-ratio of G10-MONO is 9,082-fold higher than that of its POLY counterpart.

Similarly, the calculated E/T-ratios of M10-MONO and M10-POLY are 4711/22=214 and 635/2364=0.2686, respectively, which means a 797-fold higher E/T-ratio of M10-MONO as compared to M10-POLY.

Figure 5:
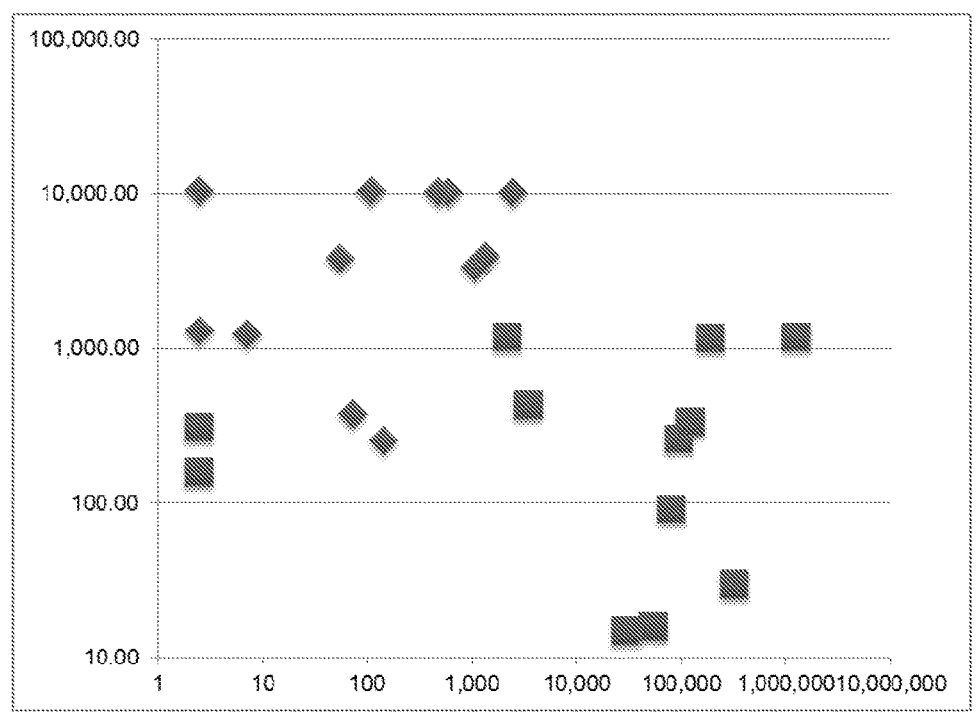
FIG. 5: E/T-plot of individual anti-H3N2 antibody titres (y-axis) versus local reaction scores 1 week post-immunization 1 plus 4 weeks post-immunization 2. Groups of 6 rabbits were immunized with H5N1 plus G10-MONO or M10-MONO (diamonds) or with G10-POLY or M10-POLY as adjuvant (squares) at Day 0 and 21. Antibody titres and local reactions were determined at Day 28 and individual data are plotted.

This difference in E/T-ratios of MONOs and POLYs is further illustrated in FIG. 5 representing individual data of animals immunized with either MONO or POLY.

In sum, in contrast to MONOs, POLYs have important disadvantages and drawbacks. The adverse in vitro effects of POLYs observed such as high hemolytic activity, rapid destabilization of emulsions and destruction of antigenic epitopes have a negative influence on the quality and stability of a vaccine containing POLY. The adverse in vivo effects of POLYs such as systemic and local adverse events have a negative effect on the in vivo performance, the E/T-ratio and hence the benefit/risk-ratio of a vaccine. Therefore, the presence of POLY in medicinal products including vaccines should be avoided as much as possible.

It has been found that carbohydrate sulphate fatty acid esters devoid of carbohydrate polysulphate fatty acid esters (POLYs) have important advantages as medicinal product and/or vaccine adjuvant. In general, the development and commercial exploitation of medicinal products containing multiple active ingredients with distinct activity profiles, is extremely complex, requires enormous efforts and harbors high risks of failure.

Safety, efficacy and quality are the three key success factors of medicinal products, including vaccines and compounds with a negative influence on one of these three factors should be avoided as much as possible. The present invention refers to carbohydrate sulphate fatty acid esters lacking polysulphate esters as promising vaccine adjuvants.

The invention claimed is:

1. A method for increasing an immune response evoked by an antigenic component comprising administering the antigenic component with an adjuvant comprising a carbohydrate ester mixture comprising a sulpholipid-carbohydrate, which is a carbohydrate substituted with at least one sulphate group and with at least one fatty acid, wherein less than 10 mole % of the carbohydrate ester mixture is substituted with more than one sulphate group, and a pharmaceutically acceptable carrier.

2. The method according to claim 1, wherein less than 5 mole % of the carbohydrate ester mixture is substituted with more than one sulphate group.

3. The method according to claim 2, wherein less than 2 mole % of the carbohydrate ester mixture is substituted with more than one sulphate group.

4. The method according to claim 1, wherein the carbohydrate ester mixture comprises 50 mole % or less, of a carbohydrate ester without sulphate groups.

5. The method according to claim 4, wherein the carbohydrate ester mixture comprises 25 mole % or less of a carbohydrate ester without sulphate groups.

6. The method according to claim 1, wherein the carbohydrate is a monosaccharide, a disaccharide, a trisaccharide, a cyclodextrin or a mixture thereof.

7. The method according to claim 6, wherein:
(a) the monosaccharide is one or more selected from the group consisting of allose, altrose, glucose, mannose, gulose, idose, galactose, talose, psicose, fructose, sorbose, tagatose, arabinose, ribose, xylose, lyxose, ribulose, xylulose and inositol;
(b) the disaccharide is one or more selected from the group consisting of sucrose, maltose, lactose, lactulose, cellobiose, trehalose, gentiobiose, turanose, isomaltulose and melibiose;
(c) the trisaccharide is one or more selected from the group consisting of raffinose, melezitose, maltotriose, isomaltotriose, kestose and negerotriose; and/or
(d) the cyclodextrin is an α-, β- or γ-cyclodextrin.

8. The method according to claim 1, wherein one of the hydroxyl-groups of the carbohydrate is substituted with the sulphate group, and wherein substantially all of the remaining hydroxyl-groups of the carbohydrate are substituted with fatty acids.

9. The method according to claim 1, wherein the fatty acid has between 6 and 18 carbon atoms.

10. The method according to claim 9, wherein the fatty acid has 8-12 carbon atoms.

11. The method according to claim 1, wherein the pharmaceutically acceptable carrier is (i) a physiological salt solution, (ii) a suspension of an insoluble organic or inorganic compound in a physiological salt solution, or (iii) an emulsion of a water-immiscible compound and a physiological salt solution.

12. The method according to claim 11, wherein the emulsion comprises an oil-in-water emulsion.

13. The method according to claim 12, wherein the oil is one or more selected from the group consisting of squalane, squalene, a plant oil and a mineral oil.

14. The method according to claim 13, wherein the oil is squalane.

15. The method according to claim 1, wherein the antigenic component is (i) a killed micro-organism, or (ii) a component or a mixture of components derived from a micro-organism, or (iii) a component or a mixture of components mimicking the relevant antigenic component of a micro-organism prepared by chemical or recombinant DNA technology, or (iv) an allergen or a host component to which a immune response is desired for therapeutic purposes.

16. A vaccine comprising:
an adjuvant comprising a carbohydrate ester mixture comprising a sulpholipid-carbohydrate, which is a carbohydrate substituted with at least one sulphate group and with at least one fatty acid, wherein less than 10 mole % of the carbohydrate ester mixture is substituted with more than one sulphate group, and a pharmaceutically acceptable carrier, and an antigenic component.

17. A vaccine according to claim 16, wherein the antigenic component is is (i) a killed micro-organism, or (ii) a component or a mixture of components derived from a micro-organism, or (iii) a component or a mixture of components mimicking the relevant antigenic component of a micro-organism prepared by chemical or recombinant DNA technology, or (iv) an allergen or a host component to which an immune response is desired for therapeutic purposes.

18. The vaccine according to claim 17, wherein the micro-organism is a bacteria, a virus or a parasite.

19. The vaccine according to claim 16, wherein less than 5 mole % of the carbohydrate ester mixture is substituted with more than one sulphate group.

20. The vaccine according to claim 19, wherein less than 2 mole % of the carbohydrate ester mixture is substituted with more than one sulphate group.

21. The vaccine according to claim 16, wherein the carbohydrate ester mixture comprises 50 mole % or less, of a carbohydrate ester without sulphate groups.

22. The vaccine according to claim 21, wherein the carbohydrate ester mixture comprises 25 mole % or less of a carbohydrate ester without sulphate groups.

23. The vaccine according to claim 16, wherein the carbohydrate is a monosaccharide, a disaccharide, a trisaccharide, a cyclodextrin or a mixture thereof.

24. The vaccine according to claim 23, wherein:
(a) the monosaccharide is one or more selected from the group consisting of allose, altrose, glucose, mannose, gulose, idose, galactose, talose, psicose, fructose, sorbose, tagatose, arabinose, ribose, xylose, lyxose, ribulose, xylulose and inositol;
(b) the disaccharide is one or more selected from the group consisting of sucrose, maltose, lactose, lactulose, cellobiose, trehalose, gentiobiose, turanose, isomaltulose and melibiose;
(c) the trisaccharide is one or more selected from the group consisting of raffinose, melezitose, maltotriose, isomaltotriose, kestose and negerotriose; and/or
(d) the cyclodextrin is an $\alpha$-, $\beta$- or $\gamma$-cyclodextrin.

25. The vaccine according to claim 16, wherein one of the hydroxyl-groups of the carbohydrate is substituted with the sulphate group, and wherein substantially all of the remaining hydroxyl-groups of the carbohydrate are substituted with fatty acids.

26. The vaccine according to claim 16, wherein the fatty acid has between 6 and 18 carbon atoms.

27. The vaccine according to claim 26, wherein the fatty acid has 8-12 carbon atoms.

28. The vaccine according to claim 16, wherein the pharmaceutically acceptable carrier is (i) a physiological salt solution, (ii) a suspension of an insoluble organic or inorganic compound in a physiological salt solution, or (iii) an emulsion of a water-immiscible compound and a physiological salt solution.

29. The vaccine according to claim 28, wherein the emulsion comprises an oil-in-water emulsion.

30. The vaccine according to claim 29, wherein the oil is one or more selected from the group consisting of squalane, squalene, a plant oil and a mineral oil.

31. The vaccine according to claim 30, wherein the oil is squalane.

32. A kit of parts comprising:
an adjuvant comprising a carbohydrate ester mixture comprising a sulpholipid-carbohydrate, which is a carbohydrate substituted with at least one sulphate group and with at least one fatty acid, wherein less than 10 mole % of the carbohydrate ester mixture is substituted with more than one sulphate group, and a pharmaceutically acceptable carrier, and
an antigenic component.

33. A process for preparing a carbohydrate ester mixture comprising a monosulphate carbohydrate fatty acid ester, wherein less than 10 mole % of the carbohydrate ester mixture is substituted with more than one sulphate group, the method comprising:
(a) esterifying a carbohydrate with a sulfonating agent and a reactive fatty acid acyl compound to obtain the carbohydrate ester mixture, and
(b) fractionating the mixture to remove the carbohydrate esters with more than one sulphate group from the carbohydrate ester mixture to obtain the mixture comprising a monosulphate carbohydrate fatty acid ester.

34. The process according to claim 33, wherein the fractionation further comprises removing of carbohydrate esters with no sulphate groups from the carbohydrate ester mixture.

* * * * *